(12) United States Patent
Miyazawa

(10) Patent No.: US 9,509,236 B2
(45) Date of Patent: Nov. 29, 2016

(54) INTEGRATED CIRCUIT APPARATUS, ULTRASOUND MEASURING APPARATUS, ULTRASOUND PROBE AND ULTRASOUND DIAGNOSIS APPARATUS

(71) Applicant: SEIKO EPSON CORPORATION, Tokyo (JP)

(72) Inventor: Takao Miyazawa, Shimosuwa-machi (JP)

(73) Assignee: Seiko Epson Corporation, Tokyo (JP)

( * ) Notice: Subject to any disclaimer, the term of this patent is extended or adjusted under 35 U.S.C. 154(b) by 253 days.

(21) Appl. No.: 14/035,284

(22) Filed: Sep. 24, 2013

(65) Prior Publication Data

US 2014/0088431 A1 Mar. 27, 2014

(30) Foreign Application Priority Data

Sep. 25, 2012 (JP) ................................ 2012-210462

(51) Int. Cl.
*H02N 2/18* (2006.01)
*B06B 1/02* (2006.01)
*A61B 8/00* (2006.01)

(52) U.S. Cl.
CPC ............ *H02N 2/181* (2013.01); *A61B 8/4483* (2013.01); *A61B 8/4494* (2013.01); *B06B 1/0207* (2013.01); *A61B 8/4405* (2013.01); *A61B 8/4427* (2013.01)

(58) Field of Classification Search
CPC .................................................. G10K 11/341
See application file for complete search history.

(56) References Cited

U.S. PATENT DOCUMENTS

| | | | |
|---|---|---|---|
| 5,537,367 A * | 7/1996 | Lockwood | H01Q 21/22 342/372 |
| 5,722,412 A | 3/1998 | Pflugrath et al. | |
| 5,893,363 A | 4/1999 | Little et al. | |
| 6,089,096 A * | 7/2000 | Alexandru | 73/626 |
| 6,120,449 A * | 9/2000 | Snyder et al. | 600/447 |
| 6,135,961 A | 10/2000 | Pflugrath et al. | |
| 6,310,831 B1 * | 10/2001 | Dillman | 367/105 |
| 6,416,475 B1 | 7/2002 | Hwang et al. | |
| 7,819,807 B2 | 10/2010 | Barnes et al. | |
| 2005/0124890 A1 | 6/2005 | Halmann et al. | |
| 2007/0016026 A1 * | 1/2007 | Thomenius et al. | 600/437 |
| 2007/0232924 A1 | 10/2007 | Karasawa | |
| 2008/0294050 A1 * | 11/2008 | Shinomura et al. | 600/459 |
| 2010/0202253 A1 * | 8/2010 | Nakamura | 367/155 |
| 2011/0046484 A1 * | 2/2011 | Adams | 600/440 |

FOREIGN PATENT DOCUMENTS

| | | |
|---|---|---|
| JP | 10-277035 A | 10/1998 |
| JP | 2003-190159 A | 7/2003 |
| JP | 2007-244415 A | 9/2007 |
| WO | 2006/006460 A1 | 1/2006 |

* cited by examiner

*Primary Examiner* — Katherine Fernandez
*Assistant Examiner* — Don N Ho
(74) *Attorney, Agent, or Firm* — Global IP Counselors, LLP

(57) ABSTRACT

An integrated circuit apparatus includes transmitting circuits TX1 to TX64, which output transmission signals with regard to channels CH1 to CH64 of an ultrasound transducer device which has a plurality of ultrasound transducer elements, and a switching circuit which performs a switching operation. The switching circuit is provided between a receiving circuit and output nodes NQ1 to NQ64 of the transmitting circuits TX1 to TX64. Then, an operation is performed where the signal transfer of the transmission signal from the transmitting circuits TX1 to TX64 to the receiving circuit is set to be not transferred in a transmitting period. A switching operation is performed where the reception signals from the channels which are selected from among the channels CH1 to CH64 are output to the receiving circuit in a receiving period.

14 Claims, 16 Drawing Sheets

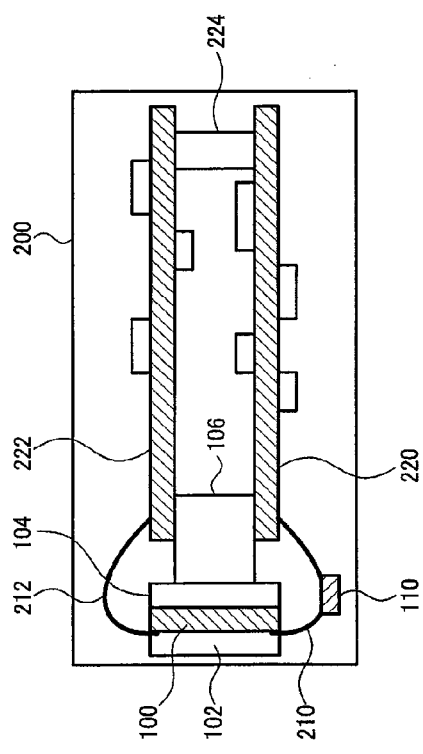
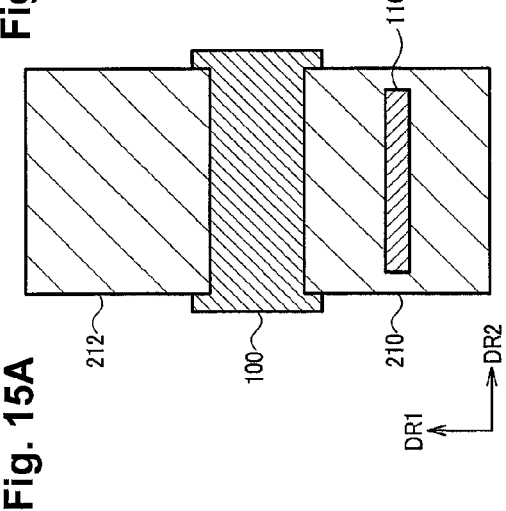
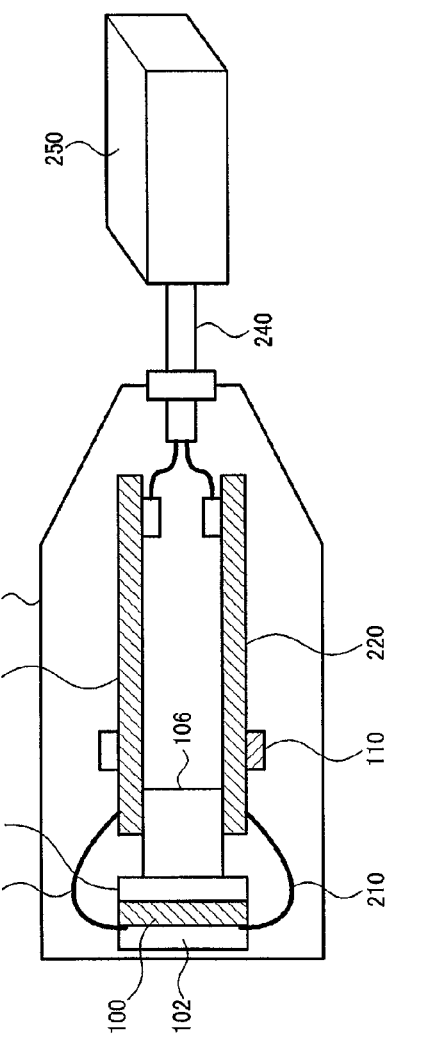
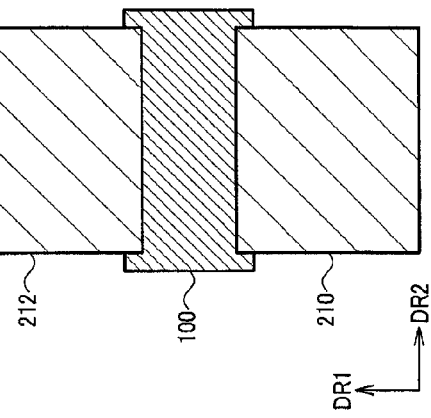

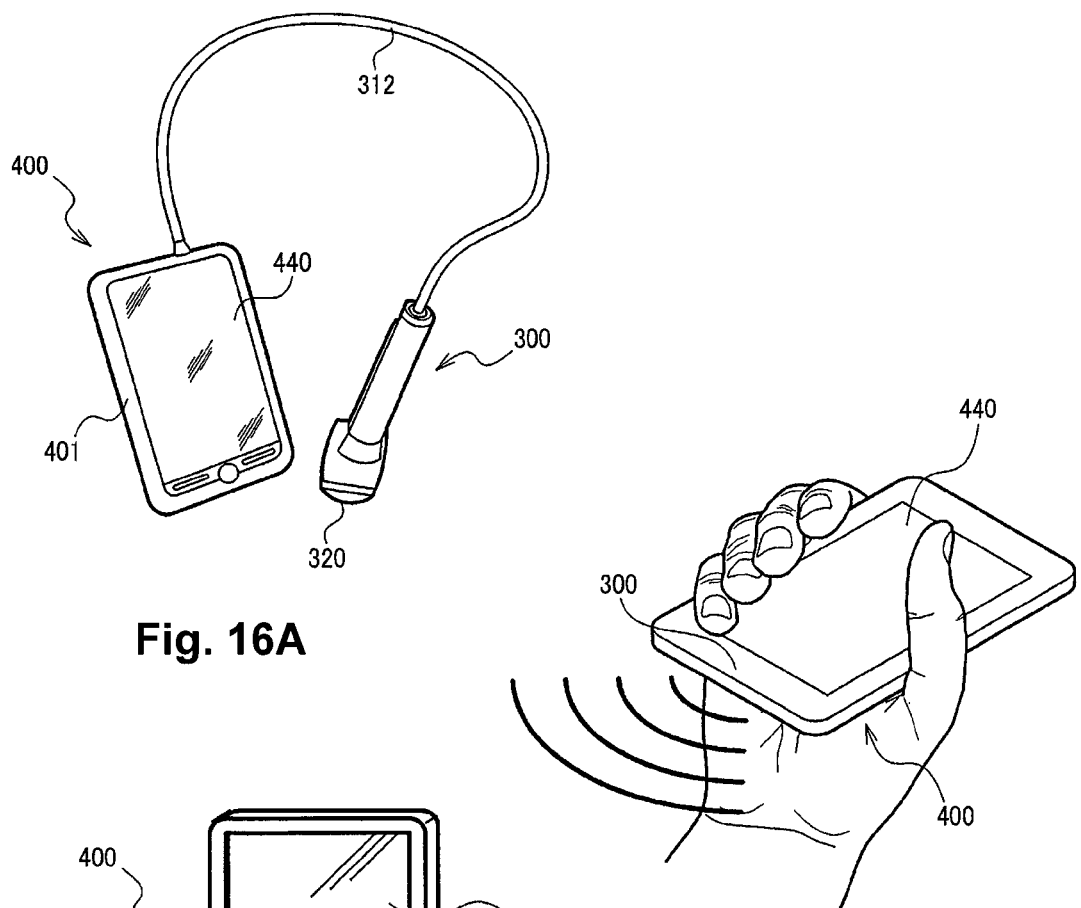
Fig. 16A
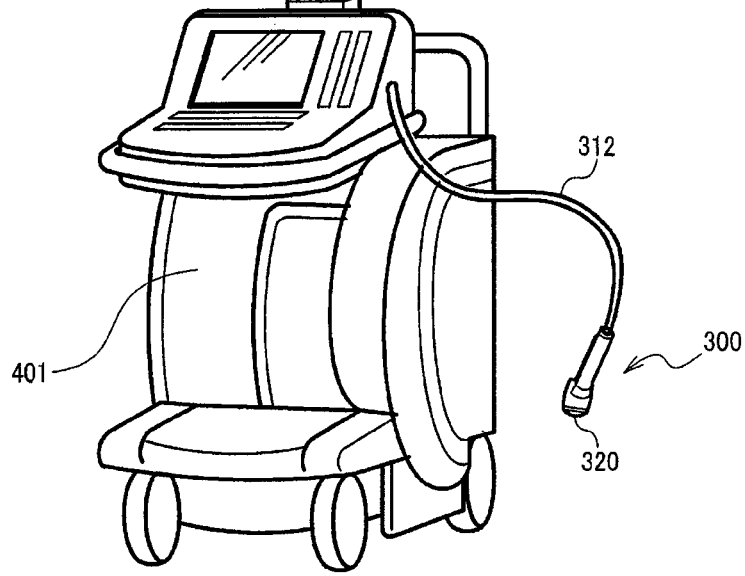
Fig. 16C
Fig. 16B

INTEGRATED CIRCUIT APPARATUS, ULTRASOUND MEASURING APPARATUS, ULTRASOUND PROBE AND ULTRASOUND DIAGNOSIS APPARATUS

CROSS-REFERENCE TO RELATED APPLICATIONS

This application claims priority to Japanese Patent Application No. 2012-210462 filed on Sep. 25, 2012. The entire disclosure of Japanese Patent Application No. 2012-210462 is hereby incorporated herein by reference.

BACKGROUND

1. Technical Field

The present invention relates to an integrated circuit apparatus, an ultrasound measuring apparatus, an ultrasound probe, an ultrasound diagnostic apparatus, and the like.

2. Related Art

As an apparatus which emits ultrasound toward an object and receives reflected waves from interfaces with different acoustic impedances in the inside of the object, there is, for example, known an ultrasound measuring apparatus for scanning the inside of a human body which is the target sample. Such ultrasound apparatuses are provided with a transmitting circuit (a pulser) which outputs transmission signals with regard to each of the channels of an ultrasound transducer device which emits ultrasound beams and a receiving circuit which receives reception signals (ultrasound echo signals) from each of the channels.

On the other hand, as the scanning mode of the ultrasound measuring apparatus, there are a linear scanning mode, a sector scanning mode, and the like. In the linear scanning mode, an operation is performed where a channel which is the target of the linear scanning is selected from among a plurality of channels of the ultrasound transducer device. Then, for example, in Japanese Unexamined Patent Application Publication No. 2007-244415, a multiplexer is provided between an output node of the transmitting circuit and the ultrasound transducer device.

SUMMARY

However, in the prior art of Japanese Unexamined Patent Application Publication No. 2007-244415, it is understood that the voltage of the transmission signal which is applied to an ultrasound transducer element decreases due to causes such as on resistance of switching elements which configure the multiplexer and there is a concern that it may not be possible to obtain the desired ultrasound sound pressure.

According to some aspects of the present invention, it is possible to provide an integrated circuit apparatus, an ultrasound measuring apparatus, an ultrasound probe, an ultrasound diagnostic apparatus and the like where efficient transferring and the like of ultrasound transmission signals to a ultrasound transducer device is possible.

One aspect of the present invention relates to an integrated circuit apparatus including a first transmitting circuit to a $K^{th}$ (where K is an integer of 2 or more) transmitting circuit, which output a transmission signal with regard to a first channel to a $K^{th}$ channel of an ultrasound transducer device which has a plurality of ultrasound transducer elements, and a switching circuit which performs a switching operation, where the switching circuit is provided between a receiving circuit and a first output node to a $K^{th}$ output node of the first transmitting circuit to the $K^{th}$ transmitting circuit, an operation is performed where the signal transfer of the transmission signal from the first transmitting circuit to the $K^{th}$ transmitting circuit to the receiving circuit is not to be transferred in a transmitting period, and a switching operation is performed where the reception signal from a channel which is selected from among the first channel to the $K^{th}$ channel is output to the receiving circuit in a receiving period.

According to one aspect of the present invention, the switching circuit is provided between the receiving circuit and the first to $K^{th}$ output nodes of the first to $K^{th}$ transmitting circuits. Then, when the first to $K^{th}$ transmitting circuits output transmission signals with regard to the first to $K^{th}$ channels of the ultrasound transducer device in the transmitting period, the switching circuit operates such that the transmission signals are not signal-transferred to the receiving circuit. Then, the switching circuit performs a switching operation such that the reception signal from the channel which is selected from among the first to $K^{th}$ channels is supplied to the receiving circuit in the receiving period.

In the one aspect of the present invention, the switching circuit is not provided between the ultrasound transducer device and the first to $K^{th}$ output nodes of the first to $K^{th}$ transmitting circuits, but between the receiving circuit and the first to $K^{th}$ output nodes. Accordingly, it is possible to input the transmission signals from the first to $K^{th}$ transmitting circuits to the first to $K^{th}$ channels of the ultrasound transducer device without going through, for example, a switching element or the like of the multiplexer. Due to this, efficient transferring and the like of the ultrasound transmission signal to the ultrasound transducer device are possible. In addition, it is also possible to prevent a situation where the transmission signal is signal-transferred to the receiving circuit due to operation of the switching circuit. Furthermore, since it is possible to supply the reception signal from the channel which is selected from among the first to $K^{th}$ channels to the receiving circuit in the receiving period, it is possible to realize an appropriate receiving process for the ultrasound reception signal.

In addition, in one aspect of the present invention, the switching circuit may perform a switching operation where the plurality of channels which are the target of linear scanning from among the first channel to the $K^{th}$ channel are sequentially shifted and selected in the receiving period in a linear scanning mode.

According to this, it is possible to supply the reception signals from the plurality of sequentially shifted and selected channels to the receiving circuit and it is possible to realize an appropriate receiving process in the linear scanning mode.

In addition, in one aspect of the present invention, the switching circuit may output the reception signal from L (where L is an integer of 2 or more with L<K) channels, which are the target of the linear scanning which are selected from among the first channel to the $K^{th}$ channel, to the first input node to the $L^{th}$ input node of the receiving circuit in the receiving period in the linear scanning mode, and the switching circuit may output the reception signal from the first channel to the $K^{th}$ channel to the first input node to the $K^{th}$ input node of the receiving circuit in the receiving period in a sector scanning mode.

According to this, it is possible to supply the reception signals from the L channels which are selected as the target of the linear scanning to the first to $L^{th}$ input nodes of the receiving circuit in the linear scanning mode. On the other hand, it is possible to supply the reception signals from the first to $K^{th}$ channels to the first to $K^{th}$ input nodes of the receiving circuit in the sector scanning mode. Accordingly, it is possible to realize both the scanning modes of the linear scanning mode and the sector scanning mode with high efficiency.

In addition, in one aspect of the present invention, a control circuit which performs switching control of the switching circuit may be included, and the switching circuit may include a first switching element to a $K^{th}$ switching element which are provided between the receiving circuit and the first output node to the $K^{th}$ output node of the first transmitting circuit to the $K^{th}$ transmitting circuit and are on-off controlled by the control circuit.

According to this, it is possible to supply the reception signal from the channel which is selected from among the first to $K^{th}$ channels to the receiving circuit by performing on-off control of the first to $K^{th}$ switching elements which are provided between the first to $K^{th}$ transmitting circuits and the first to $K^{th}$ output nodes.

In addition, in one aspect of the present invention, the first output node to the $K^{th}$ output node may be grouped into a first output node group to an $M^{th}$ (where L and M are integers of 2 or more with L<K and M<K) output node group where each of the output node groups is configured by L output nodes, the first switching element to the $K^{th}$ switching element may be grouped into a first switching element group to an $M^{th}$ switching element group where each of the switching element groups is configured by L switching elements, and an $i^{th}$ (1≤i≤M) switching element group among the first switching element group to the $M^{th}$ switching element group may be provided between an $i^{th}$ output node group among the first output node group to the $M^{th}$ output node group and the first input node to the $L^{th}$ input node of the receiving circuit.

According to this, it is possible to supply the reception signal from the channel which is selected from among the first to $K^{th}$ channels to the receiving circuit by performing on-off control of the $i^{th}$ switching element group which is provided between the $i^{th}$ output node group with L output nodes and the first to $L^{th}$ input nodes.

In addition, in one aspect of the present invention, the control circuit may perform switching control which turns off the first switching element to the $K^{th}$ switching element in the transmitting period, and the control circuit may perform switching control which sequentially shifts and selects L switching elements which are the target of the linear scanning from among the first switching element to the $K^{th}$ switching element and turns on the selected L switching elements in the receiving period.

According to this, it is possible for the transmission signal to not be transferred to the receiving circuit due to turning off the first to $K^{th}$ switching elements in the transmitting period. On the other hand, it is possible to realize selection of the reception channels in the linear scanning by sequentially shifting, selecting, and turning on the L switching elements in the receiving period.

In addition, in one aspect of the present invention, there may be included a first transmission and reception switching circuit to a $K^{th}$ transmission and reception switching circuit which are provided between the first output node to the $K^{th}$ output node and the first switching element to the $K^{th}$ switching element and are for setting the signal transfer of the transmission signal from the first transmitting circuit to the $K^{th}$ transmitting circuit to the receiving circuit to be not transferred in the transmitting period, and the control circuit may perform switching control which sequentially shifts and selects L switching elements which are the target of the linear scanning from among the first switching element to the $K^{th}$ switching element and turns on the selected L switching elements in the receiving period.

According to this, it is possible for the transmission signal to not be transferred to the receiving circuit using the first to $K^{th}$ transmission and reception switching circuits in the transmitting period. On the other hand, it is possible to realize selection of the reception channels in the linear scanning by sequentially shifting, selecting, and turning on the L switching elements in the receiving period.

In addition, in one aspect of the present invention, there may be included a first amplification circuit to an $L^{th}$ amplification circuit which perform signal amplification of the reception signal from the selected L switching elements and output the reception signal after signal amplification to the first input node to the $L^{th}$ input node of the receiving circuit.

According to this, it is possible to amplify the reception signals from the selected L switching elements using the first to $L^{th}$ amplification circuits and supply the reception signals to the first to $L^{th}$ input nodes of the receiving circuit. Due to this, it is possible to reduce signal deterioration and the like due to causes such as parasitic capacitance.

In addition, in one aspect of the present invention, the switching circuit may include a scanning mode switching circuit, the first switching element to the $K^{th}$ switching element may be provided between the first output node to the $K^{th}$ output node and a first connection node to a $K^{th}$ connection node, the first connection node to the $K^{th}$ connection node may be grouped into a first connection node group to an $M^{th}$ connection node group where each of the connection node groups is configured by L connection nodes, and the scanning mode switching circuit may perform a switching operation where each of the connection nodes of the first connection node group are connected with regard to connection nodes which correspond to each of the connection nodes among the second connection node group to the $M^{th}$ connection node group in the linear scanning mode.

According to this, it is possible to realize selection of the reception channels in the linear scanning by connecting each of the connection nodes of the first connection node group and the corresponding connection nodes among the second to $M^{th}$ connection node groups using the scanning mode switching circuit in the linear scanning mode.

In addition, in one aspect of the present invention, the first transmitting circuit to the $K^{th}$ transmitting circuit may output the transmission signals to the first channel to the $K^{th}$ channel without going through the multiplexer.

According to this, it is possible to suppress signal loss of the transmission signals due to causes such as the on resistance of the switching elements of the multiplexer to a minimum.

In addition, in one aspect of the present invention, each of the ultrasound transducer elements of the plurality of ultrasound transducer elements may have a diaphragm which closes off each opening of a plurality of openings which are formed in the substrate and a piezoelectric element section which is provided with a lower electrode, an upper electrode, and a piezoelectric film which are provided on the diaphragm.

In the ultrasound transducer elements with a thin film piezoelectric format, the parasitic capacitance between the first to $K^{th}$ transmitting circuits and the ultrasound transducer elements is a problem since the parasitic capacitance is large, but it is possible to solve this problem using the one aspect of the present invention.

In addition, another aspect of the present invention relates to an ultrasound measuring apparatus which includes any of the integrated circuit apparatuses described above.

In addition, in another aspect of the present invention, the integrated circuit apparatus may be mounted on a flexible printed circuit which is connected with the ultrasound transducer device.

In addition, in another aspect of the present invention, there may be included a circuit substrate where a receiving circuit is mounted, and the flexible printed circut may be connected with the ultrasound transducer device and the circuit substrate.

In addition, another aspect of the present invention relates to an ultrasound probe which includes any of the ultrasound measuring apparatuses described above.

In addition, another aspect of the present invention relates to an ultrasound diagnostic apparatus which includes any of the ultrasound measuring apparatuses described above and a display section which displays an image.

BRIEF DESCRIPTION OF THE DRAWINGS

Referring now to the attached drawings which form a part of this original disclosure:

FIG. 15A to FIG. 15D are explanatory diagrams of specific embodiments of ultrasound measuring apparatuses.

FIG. 16A to FIG. 16C are examples of specific device configurations of the ultrasound measuring apparatus.

DETAILED DESCRIPTION OF EXEMPLARY EMBODIMENTS

Below, preferable embodiments of the present invention will be described in detail. Here, the present embodiment which is described below does not disadvantageously limit the contents of the present invention which are described in the scope of the claims and it is not always the case that the configurations which are described in the present embodiment are essential as the solving means of the present invention.

1. Comparative Example

Figure 1:
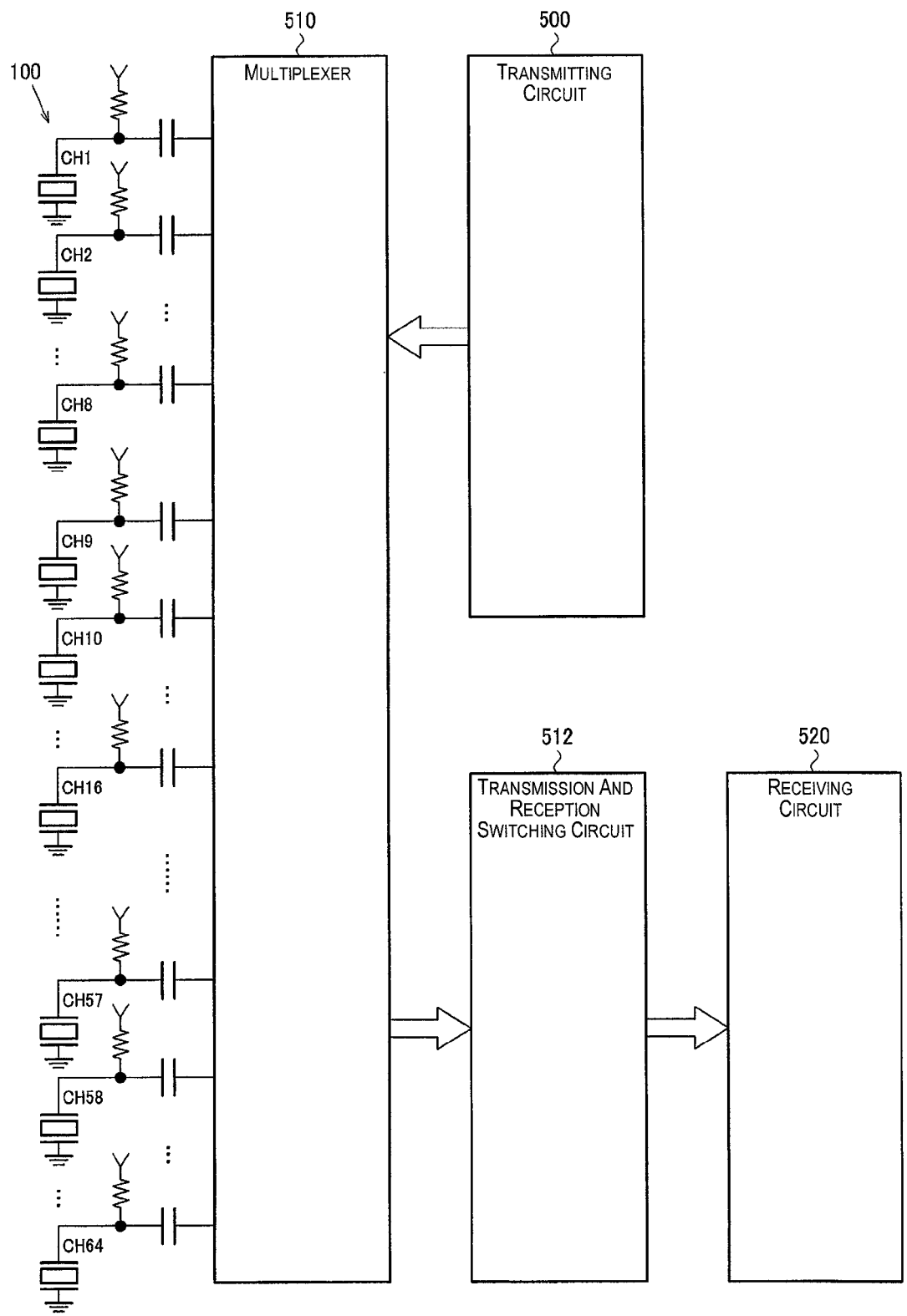
FIG. 1 is a configuration example of a comparative example of the present embodiment.

FIG. 1 illustrates a configuration example of an ultrasound measuring apparatus which is a comparative example of the present embodiment. The ultrasound measuring apparatus has an ultrasound transducer device 100, a transmitting circuit 500, a multiplexer 510, a transmission and reception switching circuit 512, and a receiving circuit 520.

In the comparative example of FIG. 1, a transmission signal from the transmitting circuit 500 which is configured by a pulser or the like is output to the ultrasound transducer device 100 via the multiplexer 510 in a transmitting period. In this case, the transmission and reception switching circuit 512 performs a circuit operation where the transmission signal from the transmitting circuit 500 is set to be not signal-transferred to the receiving circuit 520.

On the other hand, a reception signal from the ultrasound transducer device 100 is input to the receiving circuit 520 via the multiplexer 510 and the transmission and reception switching circuit 512 in a receiving period.

In FIG. 1, for example, the multiplexer 510 performs an operation where the channel which is the target of the linear scanning is selected from among channels CH1 to CH64 in a linear scanning mode in FIG. 4A to be described later.

For example, first, the channels CH1 to CH8 are selected as the target of the linear scanning and the transmission signal (a transmission pulse) from the transmitting circuit 500 is output to the channels CH1 to CH8 of the ultrasound transducer device 100 via the multiplexer 510. Then, the reception signals from the channels CH1 to CH8 are input to the receiving circuit 520 via the multiplexer 510 and the transmission and reception switching circuit 512. The receiving circuit 520 performs receiving processes such as signal amplification, gain adjustment, filter processing, and A/D conversion of the reception signal.

Next, the channels CH2 to CH9 are selected as the target of the linear scanning and the transmission signal from the transmitting circuit 500 is output to the channels CH2 to CH9. Then, the reception signals from the channels CH2 to CH9 are input to the receiving circuit 520. In this manner, the selection of the channels is sequentially performed using the linear scanning, and the channels CH57 to CH64 are selected last of all.

However, in the comparative example in FIG. 1, it is understood that the voltage of the transmission signal which is applied to an ultrasound transducer element in the ultrasound transducer device 100 decreases due to causes such as the on resistance of the switching elements which configure the multiplexer 510 and there is a concern that it may not be possible to obtain the desired ultrasound sound pressure.

Figure 2:
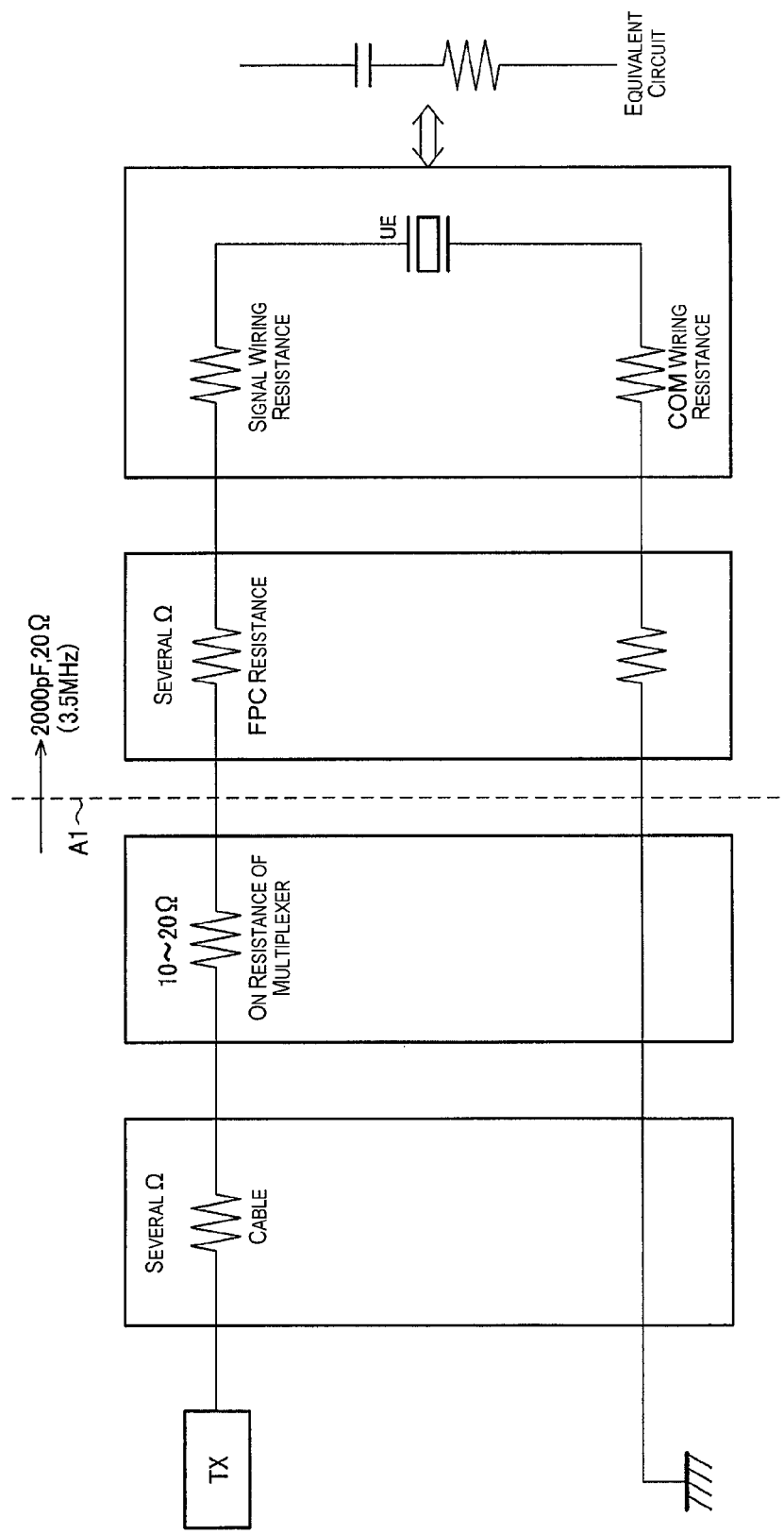
FIG. 2 is an explanatory diagram of problems in the comparative example.

For example, in the ultrasound transducer element with the thin film piezoelectric format to be described later, the impedance at the frequency to be used is small since the capacity component of the element is large compared to a bulk format. Accordingly, when the ultrasound transducer element with the thin film piezoelectric format is driven using a transmitting circuit for use in the bulk format, there are problems in that it is easy for the ultrasound transducer element to be influenced by a resistance component which comes onto the driving line. As a result, in order to obtain the desired ultrasound sound pressure, it is necessary to increase the driving voltage in order to counteract the influence of the resistance component. FIG. 2 is a diagram illustrating a state of a resistance component which comes onto a transmission line.

For example, in the transmission line, in the measurement result (frequency=3.5 MHz) in a case of viewing from A1 in FIG. 2, the impedance at 3.5 MHz is approximately 20Ω since the capacitance value is, for example, approximately 2000 pF. Here, the cable resistance is several Ω, the on resistance of the switching element of the multiplexer is 10 to 20Ω, and the wiring resistance of the FPC (the flexible printed circut) is several Ω. The voltage which is applied to the ultrasound transducer element (UE) due to the resistance component of the transmission line is half or less of the voltage of the transmission signal which is output by the transmitting circuit. In this manner, when the voltage which is applied to the ultrasound transducer element decreases, it is not possible to obtain the desired ultrasound sound pressure as a result.

Then, as shown in FIG. 2, it is understood that the main factor in the decrease in the voltage which is applied to the ultrasound transducer element is the on resistance of the multiplexer (the on resistance of the switching element). For example, in the case of the bulk format, increasing the voltage of the transmission signal of the transmitting circuit is comparatively easy since the impedance at the frequency to be used is large since the capacity component of the ultrasound transducer element is also small compared to the thin film piezoelectric format. Accordingly, it does not cause much of a problem even when the on resistance of the multiplexer is interposed between the transmitting circuit and the ultrasound transducer element.

In contrast, in the thin film piezoelectric format, the capacity component of the ultrasound transducer element is large. In addition, in a case where the transmitting circuit is built into a CMOS integrated circuit apparatus (IC), there is a limitation in that it is not possible to substantially increase the voltage of the transmission signal due to the limit of the CMOS high breakdown voltage process. For example, in a case where the voltage of the transmission signal is set to 10 to 12 V using a CMOS high breakdown voltage process with a breakdown voltage of approximately 15 V, the voltage which is applied to the ultrasound transducer element is, for example, approximately 5 to 6 V due to a main factor of the on resistance of the multiplexer. Accordingly, the voltage which is applied to the ultrasound transducer element is too low and it is not possible to obtain the desired ultrasound sound pressure. In this case, a method, where a CMOS high breakdown voltage process with a higher breakdown voltage is used, may be considered, but since transistors with a higher breakdown voltage are used according to this method, the layout area of the transmitting circuits and the like which are configured by such transistors to increase and there is a tendency for the scale of the circuit area of the integrated circuit apparatus to increase.

Figure 3:
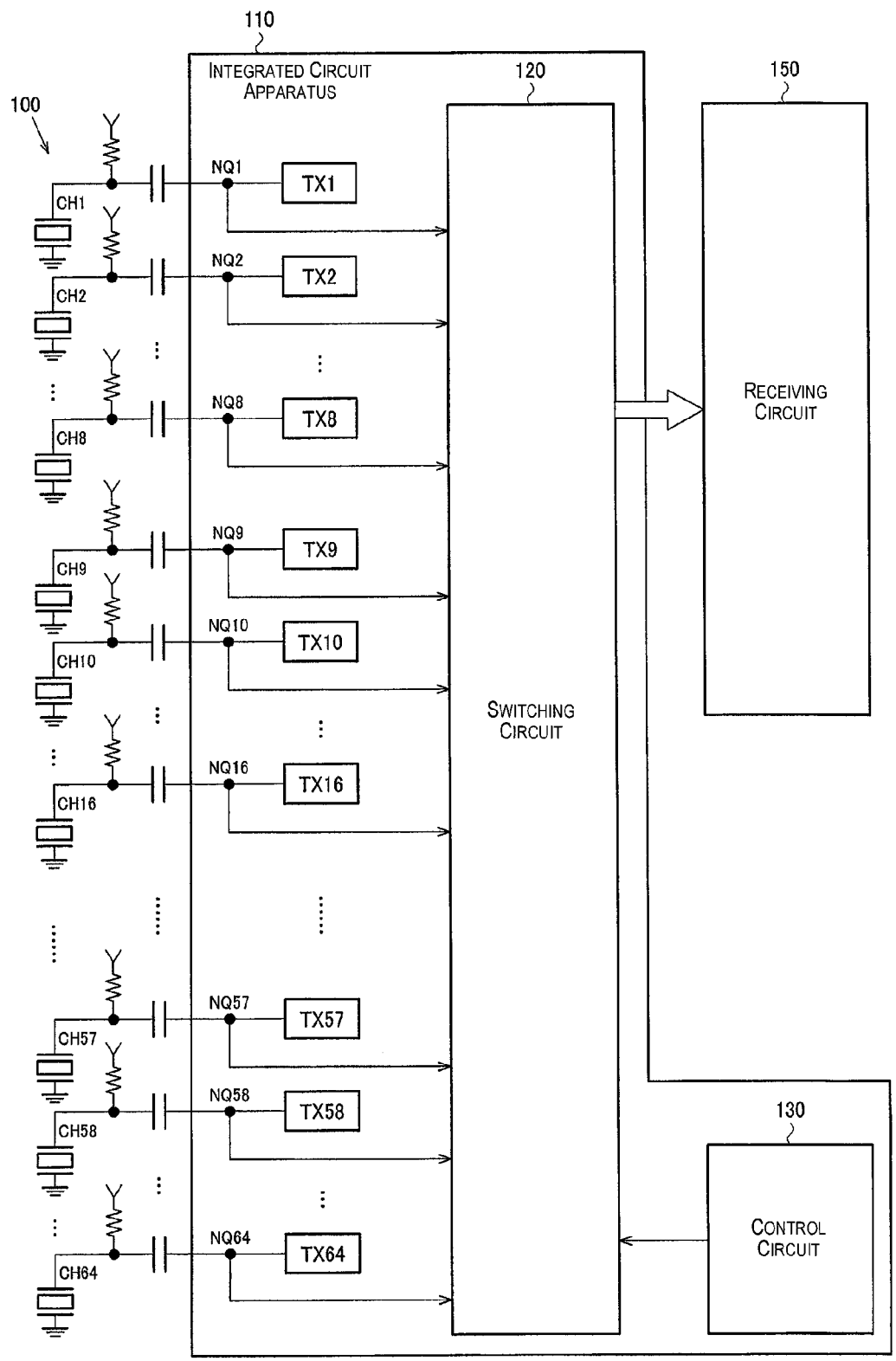
FIG. 3 is a configuration example of an integrated circuit apparatus and an ultrasound measuring apparatus of the present embodiment.

2. Configuration of Integrated Circuit Apparatus and Ultrasound Measuring Apparatus FIG. 3 illustrates a specific configuration example of an integrated circuit apparatus and an ultrasound measuring apparatus of the present embodiment. An integrated circuit apparatus 110 of the present embodiment includes transmitting circuits TX1 to TX64 and a switching circuit 120 which performs a switching operation. In addition, it is possible to include a control circuit 130 which controls the transmitting circuits TX1 to TX64 and the switching circuit 120. In addition, the ultrasound measuring apparatus includes the integrated circuit apparatus 110. In addition, it is possible to include the ultrasound transducer device 100 which has a plurality of ultrasound transducer elements, a receiving circuit 150, and the like. Here, the integrated circuit apparatus and the ultrasound measuring apparatus of the present embodiment are not limited to the configuration in FIG. 3, and various modifications which omit a portion of the constituent components, substitute with other constituent components, add other constituent components, or the like are possible.

The ultrasound transducer device 100 has a plurality of ultrasound transducer elements (an ultrasound element array) and a substrate where a plurality of openings are arranged in an array formation. Each of the ultrasound transducer elements of the plurality of ultrasound transducer elements has a diaphragm which closes off each of the openings of the plurality of openings and a piezoelectric element section which is provided with a lower electrode, an upper electrode, and a piezoelectric film which are provided on the diaphragm. The details of the ultrasound transducer device 100 will be described later. Here, it is possible to adopt a transducer of a type which uses a piezoelectric element (a thin film piezoelectric element) which will be described later as the ultrasound transducer device 100, but the present embodiment is not limited to this. For example, a transducer of a type which uses capacitive elements such as c-MUT (Capacitive Micro-machined Ultrasonic Transducers) or the like may be adopted.

The transmitting circuits TX1 to TX64 (broadly defined as first to $K^{th}$ transmitting circuits, where K is an integer of 2 or more) output transmission signals with regard to channels CH1 to CH64 (broadly defined as first to $K^{th}$ channels) of the ultrasound transducer device 100. For example, the transmitting circuits TX1 to TX64 are configured by pulsers or the like which output ultrasound pulse signals as the transmission signals. In addition, the channels CH1 to CH64 are equivalent to the terminals and signal lines of the ultrasound transducer device 100 where the ultrasound transmission signals are input and where the reception signals are output.

Here, a case where the number of channels is 64 (K=64) will be described below as an example, but the present embodiment is not limited to this and the number of channels may be less than or greater than 64. In addition, the capacitors and resistors for AC coupling and bias point adjustment of the signal are provided as external components on the integrated circuit apparatus 110 in FIG. 3, but at least one of the capacitors and resistors may be built into the integrated circuit apparatus 110.

The switching circuit 120 (the multiplexer) is a circuit which is controlled by the control circuit 130 and performs the switching operation. In the present embodiment, the switching circuit 120 is provided between the receiving circuit 150 and output nodes NQ1 to NQ64 (broadly defined as first to $K^{th}$ output nodes) of transmitting circuits TX1 to TX64 (first to $K^{th}$ transmitting circuits). In detail, one end of the switching circuit 120 is electrically connected with the output nodes NQ1 to NQ64 of the transmitting circuits TX1 to TX64. The other end of the switching circuit 120 is electrically connected with the receiving circuit 150 which is outside of the integrated circuit apparatus 110.

For example, in the comparative example in FIG. 1, the multiplexer 510 is provided between the ultrasound transducer device 100 and the output nodes of the transmitting circuit 500. In contrast, in the present embodiment in FIG. 3, the multiplexer does not exist and the switching circuit 120 is provided instead between the receiving circuit 150 and the output nodes NQ1 to NQ64 of the transmitting circuits TX1 to TX64. Then, the transmitting circuits TX1 to TX64 output the transmission signals with regard to the channels CH1 to CH64 of the ultrasound transducer device 100 without going through the multiplexer.

Then, the switching circuit 120 in the present embodiment performs an operation where the signal transfer of the transmission signal from the transmitting circuits TX1 to TX64 to the receiving circuit 150 is not transferred in the transmitting period. That is, an operation is performed to prevent (suppress) transfer of the transmission signals from the transmitting circuits TX1 to TX64 to the receiving circuit 150. In other words, the switching circuit 120 sets the reception signal to be transferred to the receiving circuit 150 in the receiving period but sets the transmission signal to be not transferred to the receiving circuit 150 in the transmitting period.

In addition, the switching circuit 120 performs a switching operation (a multiplexer operation) where the reception signals from the channels (at least one channel) which are selected from among the channels CH1 to CH64 are output to the receiving circuit 150 in the receiving period. That is, a predetermined number of channels (reception channels) are selected from the plurality of channels CH1 to CH64 and the reception signals from the selected channels are output to the receiving circuit 150.

Figure 4A:
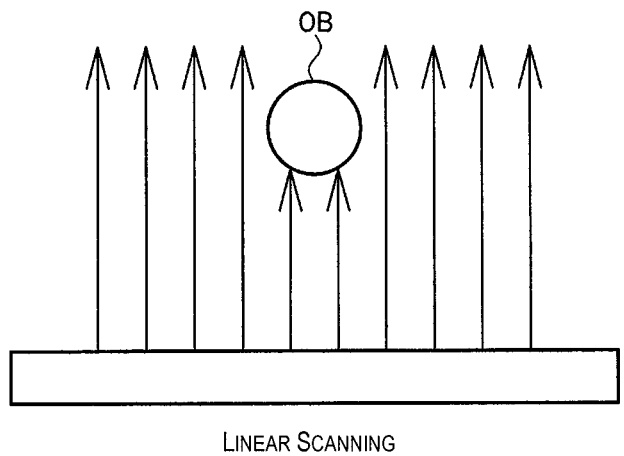
FIG. 4A and FIG. 4B are explanatory diagrams of a linear scanning mode and a sector scanning mode.
Figure 4B:
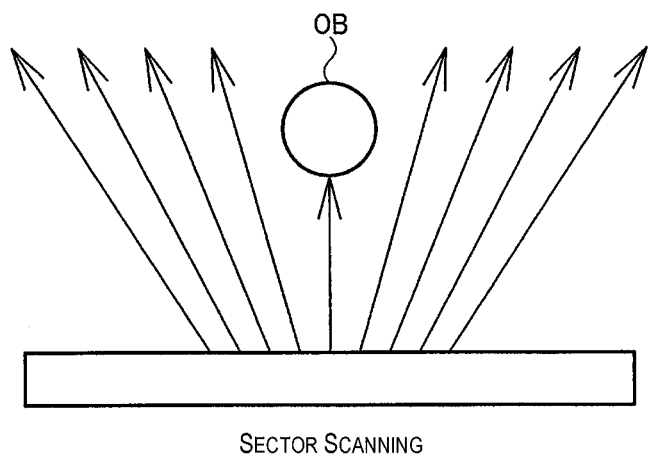

For example, as the scanning modes of the ultrasound measuring apparatus, there are the linear scanning mode shown in FIG. 4A and the sector scanning mode shown in FIG. 4B. The switching circuit 120 performs a switching operation where the plurality of channels which are the target of the linear scanning from among the channels CH1 to CH64 are sequentially shifted (for example, sequentially shifted one channel at a time) and selected in the receiving period in the linear scanning mode in FIG. 4A.

Taking the examples of FIG. 5, FIG. 7, FIG. 8, and FIG. 10 which will be described later, the switching circuit 120 performs a multiplexer operation where the reception signals from eight (broadly defined as L, where L is an integer of 2 or more with L<K) channels which are the target of the linear scanning which are selected from among the channels CH1 to CH64 are output to input nodes NI1 to NI8 (broadly defined as first to $L^{th}$ input nodes) of the receiving circuit 150 in the receiving period in the linear scanning mode in FIG. 4A.

On the other hand, the switching circuit 120 performs a switching operation where reception signals from the channels CH1 to CH64 are output to the input nodes NI1 to NI64 (broadly defined as first to $K^{th}$ input nodes) of the receiving circuit 150 in the receiving period in the sector scanning mode in FIG. 4B.

In detail, the switching circuit 120 first selects the channels CH1 to CH8 (first to $L^{th}$ channels) among the channels CH1 to CH64 (first to $K^{th}$ channels) as the channels which are the linear scanning target in the receiving period in the linear scanning mode. Due to this, the reception signals from the channels CH1 to CH8 are output to the receiving circuit 150. Next, the switching circuit 120 selects the channels CH2 to CH9 (second to $L+1^{th}$ channels) as the channels which are the linear scanning target. Due to this, the reception signals from the channels CH2 to CH9 are output to the receiving circuit 150. In the same manner, the switching circuit 120 then sequentially shifts the channels one at a time and selects the channels such as the channels CH3 to CH10 (third to $L+2^{th}$ channels) and then the channels CH4 to CH11 (fourth to $L+3^{th}$ channels). Then, the channels CH57 to CH64 ($K-L+1^{th}$ to $K^{th}$ channel) are selected last of all, and due to this, the reception signals from the channels CH57 to CH64 are output to the receiving circuit 150.

On the other hand, the switching circuit 120 outputs the reception signals from the channels CH1 to CH64 to the input nodes NI1 to NI64 (refer to FIG. 10) of the receiving circuit 150 in the receiving period in the sector scanning mode. That is, the reception signals from all of the channels CH1 to CH64 where the transmission signal is input are output as is to the receiving circuit 150. Here, it is not necessary for all of the channels CH1 to CH64 of the ultrasound transducer device 100 to be used in transmitting and receiving. For example, a method may also be considered where 48 channels from channel CH9 to channel CH56 are used in the transmission and all of the channels from channel CH1 to channel CH64 are used in the receiving, or the like. This method is a method where the opening width is changed in transmitting and receiving and it is also possible to apply the present invention to this method.

The control circuit 130 performs various types of control on the integrated circuit apparatus 110. For example, the transmission timing and the like of the transmission signals of the transmitting circuits TX1 to TX64 are controlled by controlling the transmitting circuits TX1 to TX64. In addition, the control circuit 130 performs switching control of the switching circuit 120 and controls the switching element of the switching circuit 120 to turn on and off. It is possible to realize the control circuit 130 using, for example, a logic circuit such as a gate array or a processor such as a CPU.

The receiving circuit 150 performs a receiving process on the reception signal (ultrasound echo signal) which is input from the ultrasound transducer device 100 via the integrated circuit apparatus 110 (the switching circuit 120). In detail, the receiving circuit 150 performs receiving processes such as signal amplification, gain adjustment, filter processing, and A/D conversion of the reception signal. It is possible to configure the receiving circuit 150 using, for example, an LNA (low noise amplifier), a PGA (programmable gain amplifier), a filter section, an A/D converter, or the like. Here, in FIG. 3, the receiving circuit 150 is provided outside the integrated circuit apparatus 110, but circuits of at least a portion of the receiving circuit 150 may be provided inside the integrated circuit apparatus 110.

Next, the operation in the present embodiment will be described in detail.

First, the transmitting circuits TX1 to TX8 among the transmitting circuits TX1 to TX64 output the transmission signals with regard to the channels CH1 to CH8 which are the linear scanning target among the channels CH1 to CH64 due to controlling by the control circuit 130 in the transmitting period of the linear scanning mode. In detail, a signal delay process for ultrasound focusing is performed with regard to the transmission signal and the transmission signals where signal delaying has been carried out are output to the channels CH1 to CH8. At this time, the switching circuit 120 performs an operation such that the transmission signals from the transmitting circuits TX1 to TX8 are not transferred to the receiving circuit 150.

Then, the switching circuit 120 performs a switching operation where the channels CH1 to CH8 which are the linear scanning target are selected in the receiving period. Due to this, the reception signals from the channels CH1 to CH8 are output to the receiving circuit 150 (the input nodes NI1 to NI8) via the switching circuit 120.

Next, the transmitting circuits TX2 to TX9 among the transmitting circuits TX1 to TX64 output transmission signals with regard to the channels CH2 to CH9 which are target of the linear scanning mode due to controlling by the control circuit 130 in the transmitting period. At this time, the switching circuit 120 performs an operation such that the transmission signals from the transmitting circuits TX2 to TX9 are not transmitted to the receiving circuit 150.

Then, the switching circuit 120 performs a switching operation where the channels CH2 to CH9 which are the linear scanning target are selected in the receiving period. Due to this, the reception signals from the channels CH2 to CH9 are output to the receiving circuit 150 via the switching circuit 120.

The transmitting circuits TX3 to TX10 output transmission signals to the channels CH3 to CH10 due to controlling by the control circuit 130 in the next transmitting period. At this time, the switching circuit 120 performs an operation such that the transmission signals from the transmitting circuits TX3 to TX10 are not transmitted to the receiving circuit 150.

Then, the switching circuit 120 performs a switching operation where the channels CH3 to CH10 which are the linear scanning target are selected in the receiving period. Due to this, the reception signals from the channels CH3 to CH10 are output to the receiving circuit 150 via the switching circuit 120.

Transmitting and receiving according to the linear scanning are sequentially performed as above and the transmitting circuits TX57 to TX64 output the transmission signals with regard to the channels CH57 to CH64 in the last transmitting period. Then, the channels CH57 to CH64 are selected and the reception signals from the channels CH57 and CH64 are output to the receiving circuit 150 in the receiving period.

On the other hand, the transmitting circuits TX1 to TX64 output the transmission signals with regard to the channels CH1 to CH64 in the transmitting period in the sector scanning mode. Then, the switching circuit 120 outputs the reception signals from the channels CH1 to CH64 as is with regard to the receiving circuit 150 (the input nodes NI1 to NI64) in the receiving period.

According to the present embodiment described above, it is possible for the transmitting circuit to drive the ultrasound transducer element by outputting the transmission signal to the ultrasound transducer device directly without going through the switching element (an analog switch) of the multiplexer. Accordingly, it is possible to prevent loss of the transmission signal due to the cause of the on resistance of the switching element, and it is possible to easily obtain the desired ultrasound sound pressure (transmission power).

That is, when the multiplexer is interposed between the output of the transmitting circuit and the ultrasound transducer device, as described in FIG. 2, the voltage which is applied to the ultrasound transducer element decreases due to causes such as the on resistance of the switching elements of the multiplexer, and it is not possible to obtain the desired ultrasound sound pressure.

In this regard, in the present embodiment, the transmission signal from the transmitting circuit is output to the ultrasound transducer device directly without going through the multiplexer as shown in FIG. 3. Accordingly, since the transmission loss is suppressed and it is possible to suppress a decrease in the voltage of the transmission signal to a minimum, it is possible to easily obtain the desired ultrasound sound pressure. In addition, since the transmission loss is suppressed, it is possible to adopt a CMOS high breakdown voltage process where the breakdown voltage is not very high, for example, approximately 15 V, as the manufacturing process of the integrated circuit apparatus. For example, it is possible to obtain the desired ultrasound sound pressure by applying an application voltage of, for example, approximately 10 V with regard to the ultrasound transducer element due to the transmission loss being suppressed to a minimum even when the transmitting circuit is formed with a high breakdown voltage process of 15 V and the transmitting circuit outputs the transmission signal with a voltage amplitude of, for example, approximately 12 V. Accordingly, for example, compared to a case where a high breakdown voltage process of 20 V or more is used, it is possible to reduce the layout area of the integrated circuit apparatus and it is possible to provide an appropriate integrated circuit apparatus in, for example, a portable ultrasound measuring apparatus or the like. In addition, by reducing the layout area of the circuit, it is possible to increase the number of transmission channels which are able to be integrated in one integrated circuit apparatus (IC) and it is possible for the entirety of the transmitting circuit to be more compact.

Then, in the present embodiment, while the transmission loss is reduced and the integrated circuit apparatus is made to be more compact in this manner, it is possible to realize the linear scanning mode and the sector scanning mode shown in FIG. 4A and FIG. 4B using the switching operation (the multiplexer operation) of the switching circuit. Then, the switching circuit is not provided between the output nodes of the transmitting circuit and the ultrasound transducer device, but between the output nodes of the transmitting circuit and the receiving circuit. Accordingly, since the on resistance of the switching element of the switching circuit does not come onto the transmission path, it is possible to effectively suppress the generation of transmission loss as in the comparative example in FIG. 1.

3. First Configuration Example

Figure 5:
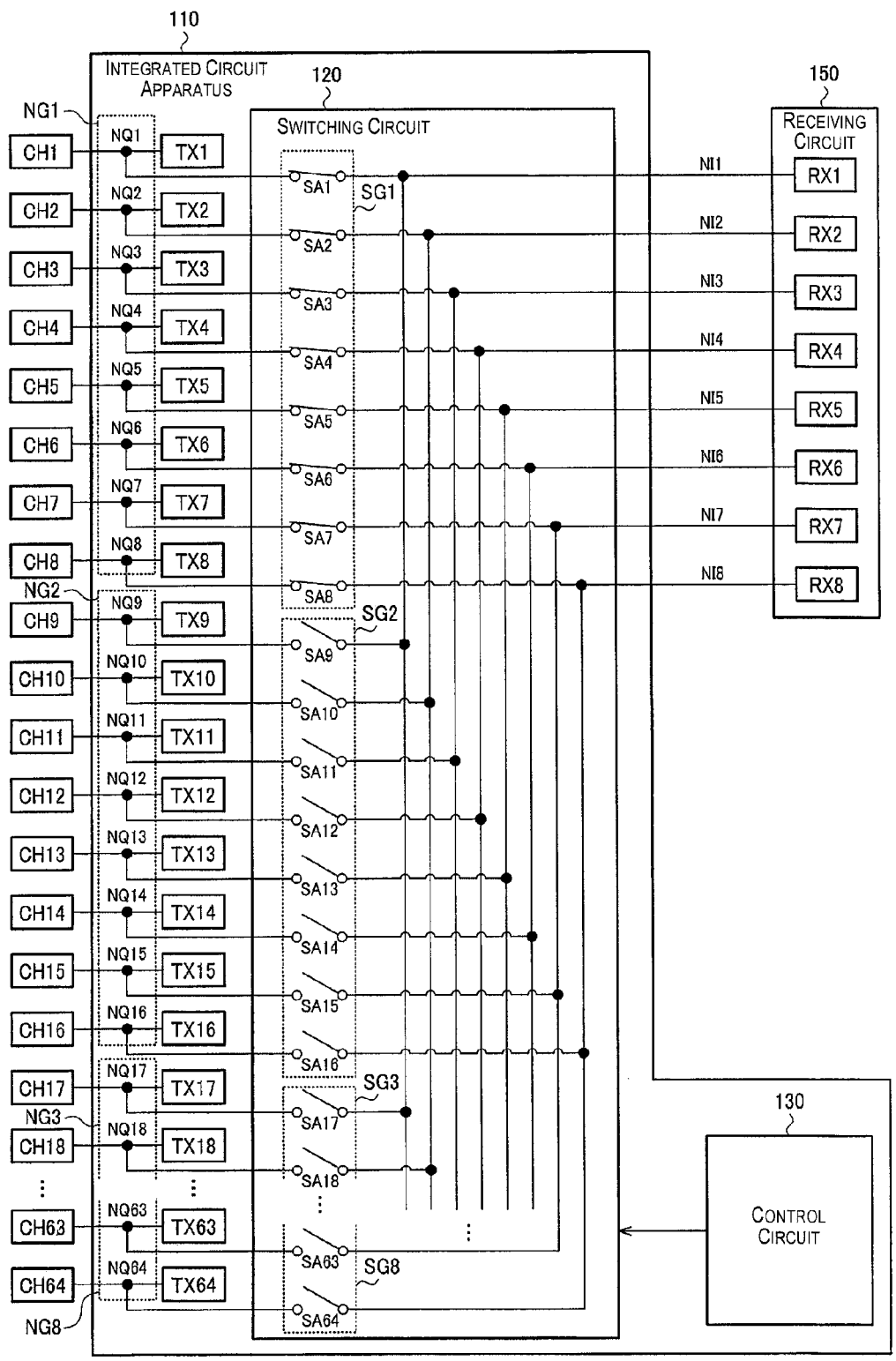
FIG. 5 is a detailed first configuration example of the present embodiment.

FIG. 5 illustrates a detailed first configuration example of the present embodiment. FIG. 5 illustrates a detailed configuration example of the switching circuit 120.

As shown in FIG. 5, the switching circuit 120 includes switching elements SA1 to SA64 (broadly defined as first to le switching elements). The switching elements SA1 to SA64 are provided between the receiving circuit 150 and the output nodes NQ1 to NQ64 (the first to $K^{th}$ output nodes) of the transmitting circuits TX1 to TX64 (the first to $K^{th}$ transmitting circuits) and are controlled to be turned on and off by the control circuit 130. It is possible for the switching elements SA1 to SA64 to be realized using, for example, an analog switch such as a transfer gate.

In detail, one end of the switching elements SA1 to SA8 is electrically connected with the output nodes NQ1 to NQ8 of the transmitting circuits TX1 to TX8 and the other end of the switching elements SA1 to SA8 is electrically connected with the input nodes NI1 to NI8 of the receiving circuit 150. The input nodes NI1 to NI8 are nodes where the reception signal is input to receiving sections RX1 to RX8 of the receiving circuit 150.

In addition, one end of the switching elements SA9 to SA16 is electrically connected with the output nodes NQ9 to NQ16 of the transmitting circuits TX9 to TX16 and the other end of the switching elements SA9 to SA16 is electrically connected with the input nodes NI1 to NI8 of the receiving circuit 150. In the same manner, one end of the switching elements SA17 to SA24 is electrically connected with the output nodes NQ17 to NQ24 of the transmitting circuits TX17 to TX24 and the other end of the switching elements SA17 to SA24 is electrically connected with the input nodes NI1 to NI8 of the receiving circuit 150. The same also applies to the connection relationship of the other switching elements SA25 to SA64.

For example, in FIG. 5, it is possible for the output nodes NQ1 to NQ64 (the first to $K^{th}$ output nodes) to be grouped into output node groups NG1 to NG8 (broadly defined as first to $M^{th}$ output node groups where L and M are integers of 2 or more with L<K and M<K and K=L×M) where each of the output node groups is configured by eight (L) output nodes. For example, the output nodes NQ1 to NQ8 belong to the output node group NG1, the output nodes NQ9 to NQ16 belong to the output node group NG2, and the output nodes NQ17 to NQ24 belong to the output node group NG3. The same also applies to the other output nodes NQ25 to NQ64.

In addition, it is also possible for the switching elements SA1 to SA64 (the first to $K^{th}$ switching elements) to be grouped into switching element groups SG1 to SG8 (broadly defined as first to $M^{th}$ switching element groups) where each of the switching element groups is configured by eight (L) switching elements. For example, the switching elements SA1 to SA8 belong to the switching element group SG1, the switching elements SA9 to SA 16 belong to the switching element group SG2, and the switching elements SA17 to SA24 belong to the switching element group SG3. The same also applies to the other switching elements SA25 to SA64.

In this case, the switching element group SG1 (broadly defined as $i^{th}$ switching element group with $1 \leq i \leq M$) among the switching element groups SG1 to SG8 is provided between the output node group NG1 (broadly defined as $i^{th}$ output node group) among the output node groups NG1 to NG8 and the input nodes NI1 to NI8 (the first to $L^{th}$ input nodes) of the receiving circuit 150. For example, one end of the switching element group SG1 is electrically connected with the output node group NG1, the other end is electrically connected with the input nodes NI1 to NI8 of the receiving circuit 150, and the switching element group SG1 performs turning on and off the connection between the output node group NG1 and the input nodes NI1 to NI8.

In addition, the switching element group SG2 (the $i^{th}$ switching element group) is provided between the output node group NG2 (the $i^{th}$ output node group) and the input nodes NI1 to NI8 of the receiving circuit 150. For example, one end of the switching element group SG2 is electrically connected with the output node group NG2, the other end is electrically connected with the input nodes NI1 to NI8 of the receiving circuit 150, and the switching element group SG2 performs turning on and off the connection between the output node group NG2 and the input nodes NI1 to NI8. The same also applies to the connection configurations of the other switching element groups SG3 to SG8.

Then, the control circuit 130 performs switching control which turns off the switching elements SA1 to SA64 in the transmitting period. Due to this, the transmission signals from the transmitting circuits TX1 to TX64 are prevented from being transferred to the receiving circuit 150.

On the other hand, the control circuit 130 sequentially shifts and selects eight (L) switching elements which are the target of the linear scanning from among the switching elements SA1 to SA64 and performs switching control which turns on the eight (L) switching elements which are selected in the receiving period of the linear scanning mode.

In detail, first, the transmitting circuits TX1 to TX8 output the transmission signals to the channels CH1 to CH8 due to controlling by the control circuit 130. At this time, the control circuit 130 turns off the switching elements SA1 to SA64. Here, since it is not preferable for noise and the like to come on when a channel which is not used in the receiving circuit 150 is connected, the switching elements SA9 to SA64, which are connected with the transmitting circuits TX9 to TX64 which do not output transmission signals, are also turned off. Here, it is also possible to turn off only the switching elements SA1 to SA8 which are connected with the transmitting circuits TX1 to TX8 which output the transmission signals. Then, the control circuit 130 turns on the eight (L) switching elements SA1 to SA8 in the subsequent receiving period. Due to this, the reception signals from the channels CH1 to CH8 are input to the input nodes NI1 to NI8 of the receiving circuit 150 via the switching elements SA1 to SA8. Then, the receiving sections RX1 to RX8 of the receiving circuit 150 perform receiving processes such as signal amplification, gain adjustment, filter processing, and A/D conversion with regard to the reception signals which are input to the input nodes NI1 to NI8.

Next, the transmitting circuits TX2 to TX9 output the transmission signals to the channels CH2 to CH9 due to controlling by the control circuit 130. At this time, the control circuit 130 turns off the switching elements SA1 to SA64 (SA2 to SA9). Then, the control circuit 130 turns on the eight switching elements SA2 to SA9 in the subsequent receiving period. Due to this, the reception signals from channels CH2 to CH8 are input to the input nodes NI2 to NI8 via the switching elements SA2 to SA8 and the reception signal from channel CH9 is input to the input node NI1 via the switching element SA9. Then, the receiving sections RX2 to RX8 perform a receiving process on the reception signals of the channels CH2 to CH8 which are input to the input nodes NI2 to NI8 and the receiving section RX1 performs a receiving process on the reception signal of the channel CH9 which is input to the input node NI1.

Next, the transmitting circuits TX3 to TX10 output the transmission signals to the channels CH3 to CH10 due to controlling by the control circuit 130. At this time, the control circuit 130 turns off the switching elements SA1 to SA64 (SA3 to SA10). The control circuit 130 turns on eight switching elements SA3 to SA10 in the subsequent receiving period. Due to this, the reception signals from the channels CH3 to CH8 are input to the input nodes NI3 to NI8 via the switching elements SA3 to SA8 and the reception signals from the channels CH9 and CH10 are input to the input nodes NI1 and NI2 via the switching elements SA9 and SA10. Then, the receiving sections RX3 to RX8 perform a receiving process on the reception signals of the channels CH3 to CH8 which are input to the input nodes NI3 to NI8 and the receiving sections RX1 and RX2 perform a receiving process on the reception signals of the channels CH9 and CH10 which are input to the input nodes NI1 and NI2.

The control circuit 130 sequentially shifts, selects, and turns on eight switching elements from among the switching elements SA1 to SA64 as above. Then, the control circuit 130 turns on the switching elements SA57 to SA64 in the last receiving period of the scanning operation. Due to this, the reception signals from the channels CH57 to CH64 are input to the input nodes NI1 to NI8 via the switching elements SA57 to SA64. Then, the receiving sections RX1 to RX8 perform a receiving process on the reception signals of the channels CH57 to CH64 which are input to the input nodes NI1 to NI8.

Figure 6:
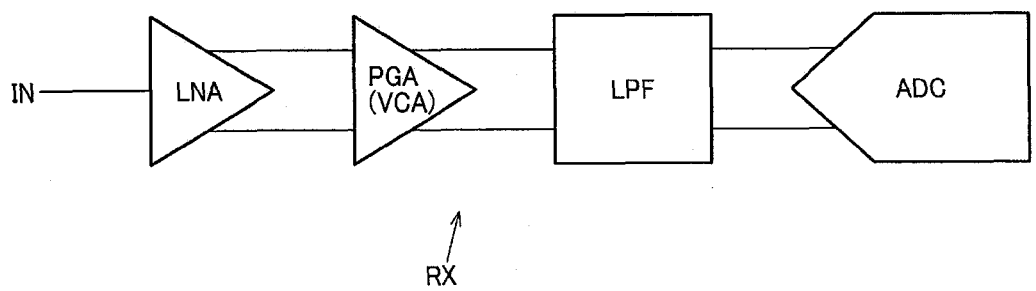
FIG. 6 is a configuration example of a receiving section of a receiving circuit.

Here, FIG. 6 illustrates a configuration example of the receiving sections RX (RX1 to RX8) in the receiving circuit 150. As shown in FIG. 6, the receiving sections RX include an LNA (low noise amplifier), a PGA (programmable gain amplifier), an LPF (filter part), and an ADC (A/D converter). The LNA performs signal amplification of the reception signal and the PGA (VCA) performs gain adjustment (voltage adjustment) of the signal after signal amplification. The LPF performs a filtering process (low pass filtering), and the ADC performs A/D conversion of the signal after the filtering process.

According to the first configuration example in FIG. 5 described above, it is possible to realize a switching operation during the scanning mode using the switching elements SA1 to SA64 in the switching circuit 120. In addition, in the first configuration example, it is possible to realize the transmission and reception switching function, where the transmission signal is prevented from being input to the receiving circuit 150, in combination with the switching operation of the switching elements SA1 to SA64. Accordingly, reducing the size, simplification, or the like of the circuit is achieved.

4. Second Configuration Example

Figure 7:
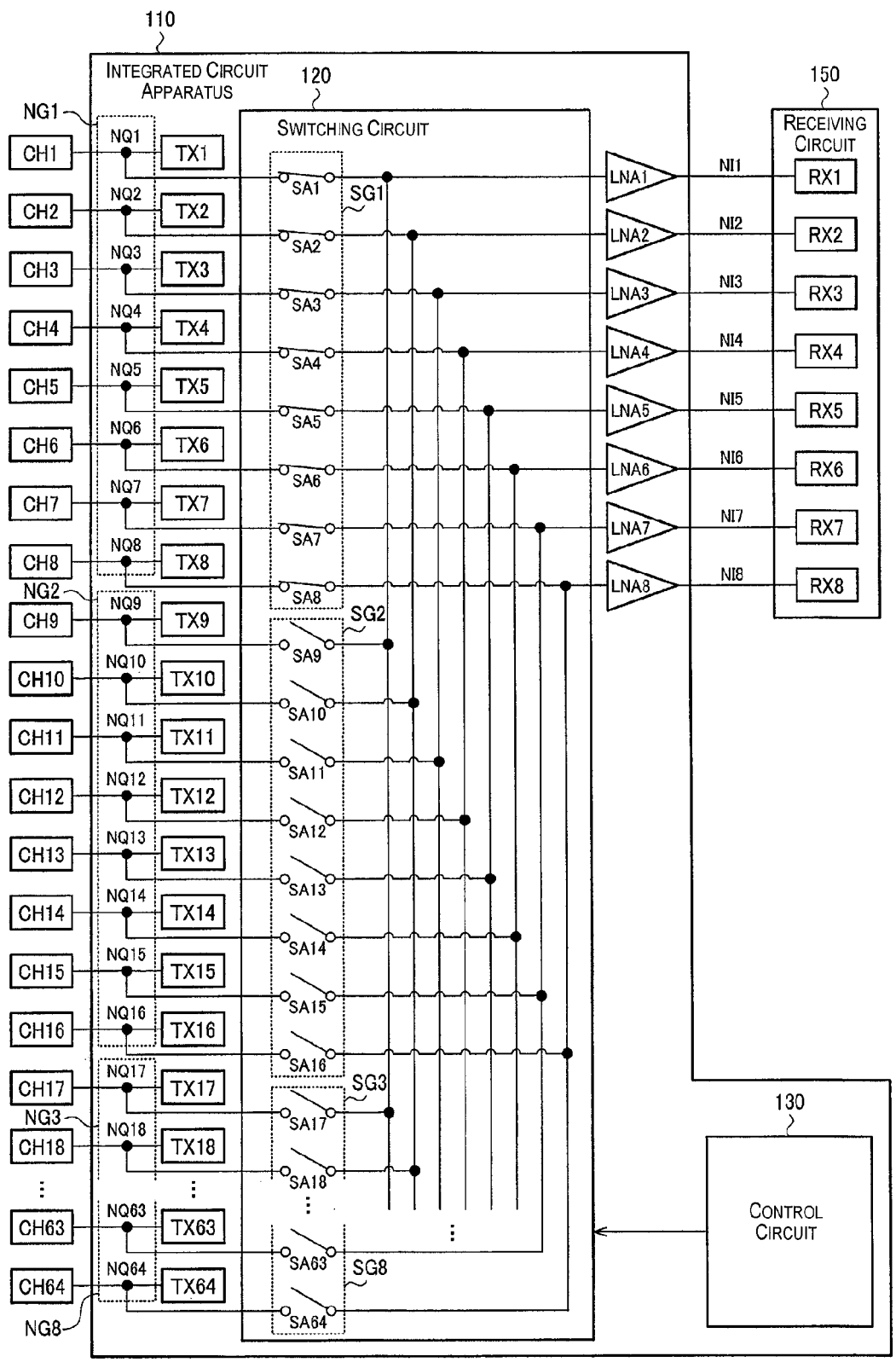
FIG. 7 is a detailed second configuration example of the present embodiment.

FIG. 7 illustrates a detailed second configuration example of the present embodiment. In the second configuration example in FIG. 7, constituent components of amplification circuits LNA1 to LNA8 are added with regard to the first configuration example in FIG. 5.

Here, the amplification circuits LNA1 to LNA8 (broadly defined as first to $L^{th}$ amplification circuits) are realized using, for example, an operational amplifier or the like which performs signal amplification with low noise. Then, the amplification circuits LNA1 to LNA8 perform signal amplification of the reception signals from the eight (L) switching elements which were selected in the linear scanning mode. Then, the reception signals after signal amplification are output to the input nodes NI1 to NI8 (the first to $L^{th}$ input nodes) in the receiving circuit 150.

For example, in a case where the switching elements SA1 to SA8 are selected and turned on in the linear scanning mode, the amplification circuits LNA1 to LNA8 perform signal amplification of the reception signals of the channels CH1 to CH8 from the switching elements SA1 to SA8. Next, in a case where the switching elements SA2 to SA9 are selected and turned on, the amplification circuits LNA2 to LNA8 perform signal amplification on the reception signals of the channels CH2 to CH8 from the switching elements SA2 to SA8 and the amplification circuit LNA1 performs signal amplification on the reception signal of the channel CH9 from the switching element SA9. Next, in a case where the switching elements SA3 to SA10 are selected and turned on, the amplification circuits LNA3 to LNA8 perform signal amplification on the reception signals of the channels CH3 to CH8 from the switching elements SA3 to SA8 and the amplification circuits LNA1 and LNA2 perform signal amplification on the reception signals of the channels CH9 and CH10 from the switching elements SA9 and SA10.

For example, when there is a large parasitic capacitance with regard to the output terminal to the receiving circuit 150 of the integrated circuit apparatus 110, there is a concern that signal deterioration such as a decrease in the amplitude of the reception signal may be generated in the first configuration example in FIG. 5. For example, in FIG. 15B which will be described later, the receiving circuit 150 is provided inside a body apparatus 250 which is connected with an ultrasound probe 200 via a cable 240. Accordingly, signal deterioration is generated due to causes such as the parasitic capacitance of the cable 240 (a coaxial cable or the like).

In this regard, in the second configuration example in FIG. 7, the amplification circuits LNA1 to LNA8 which have the ability to drive signals are provided and the reception signals are amplified by the amplification circuits LNA1 to LNA8. Accordingly, it is possible to suppress the signal deterioration such as a decrease in the amplitude of the reception signals to a minimum even in a case where there is a large parasitic capacitance with regard to the output terminals to the receiving circuit 150 in the integrated circuit apparatus 110.

5. Third Configuration Example

Figure 8:
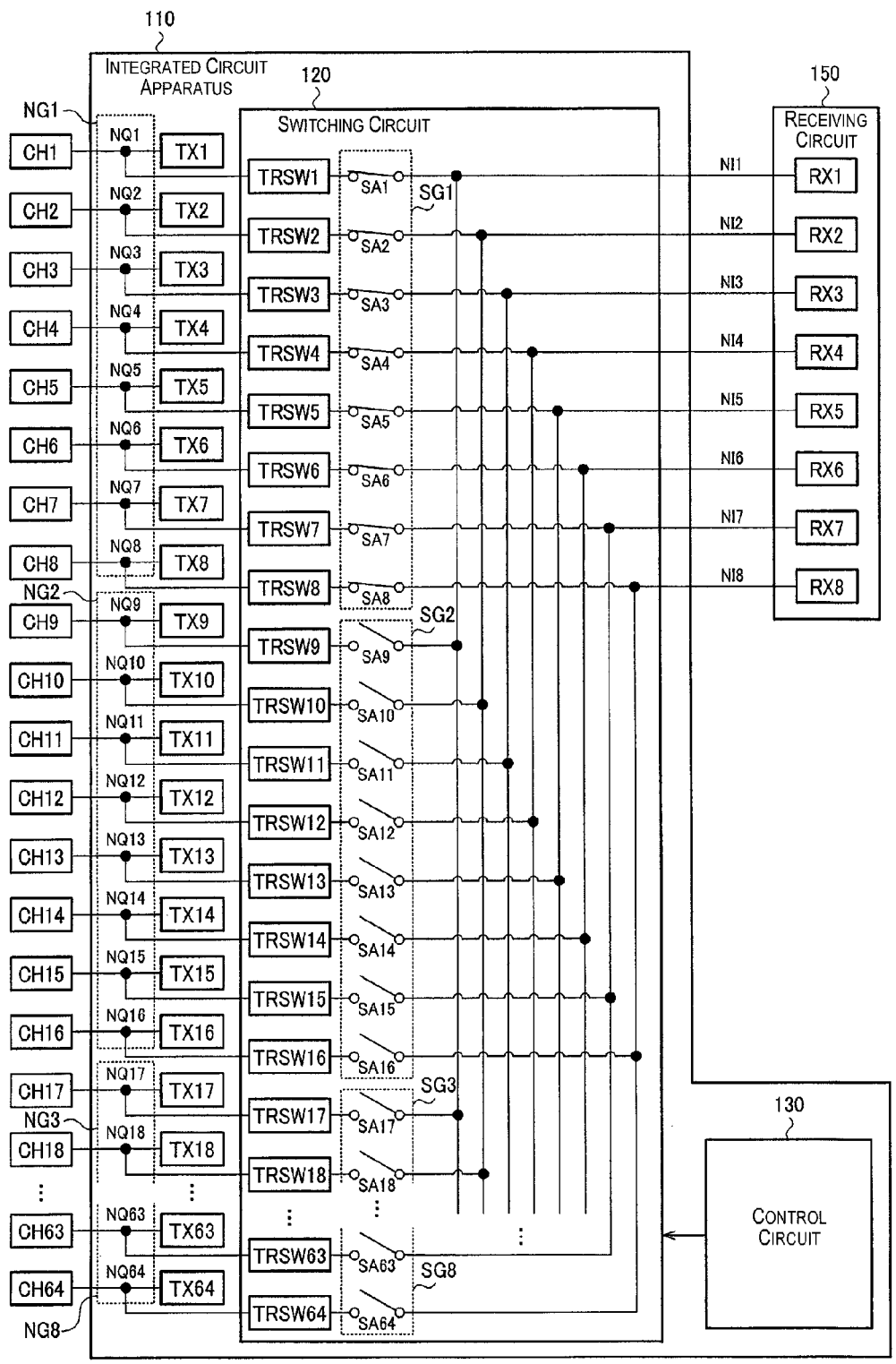
FIG. 8 is a detailed third configuration example of the present embodiment.

FIG. 8 illustrates a detailed third configuration example of the present embodiment. In the third configuration example in FIG. 8, constituent components of transmission and reception switching circuits TRSW1 to TRSW64 are added with regard to the first configuration example in FIG. 5.

The switching circuit 120 in FIG. 8 has the transmission and reception switching circuits TRSW1 to TRSW64 (broadly defined as first to $K^{th}$ transmission and reception switching circuits). The transmission and reception switching circuits TRSW1 to TRSW64 are provided between the output nodes NQ1 to NQ64 (the first to $K^{th}$ output nodes) and the switching elements SA1 to SA64 (the first to $K^{th}$ switching elements). For example, one end of the transmission and reception switching circuits TRSW1 to TRSW64 is electrically connected with the output nodes NQ1 to NQ64 of the transmitting circuits TX1 to TX64 and the other end of the transmission and reception switching circuits TRSW1 to TRSW64 is electrically connected with one end of the switching elements SA1 to SA64.

Then, the transmission and reception switching circuits TRSW1 to TRSW64 set the signal transfer of the transmission signal from the transmitting circuits TX1 to TX64 to the receiving circuit 150 to be not transferred in the transmitting period. That is, a circuit operation is performed such that the transmission signals are not transferred to the receiving circuit 150 in the transmitting period. In the first configuration example in FIG. 5, the transmission and reception switching function where the transmission signals are prevented from being input to the receiving circuit 150 is realized by turning off the switching elements SA1 to SA64 in the transmitting period. In contrast, in the third configuration example in FIG. 8, the transmission and reception switching function described above is realized using the transmission and reception switching circuits TRSW1 to TRSW64 which are provided at the front stage side of the switching elements SA1 to SA4. Then, also in the third configuration example, the control circuit 130 performs switching control where the eight (L) switching elements which are the target of the linear scanning are sequentially shifted and selected from among the switching elements SA1 to SA64 and the selected switching elements are turned on in the receiving period. By doing this, it is possible to realize the transmission and reception switching function of the switching circuit 120 and the linear scanning function.

Figure 9:
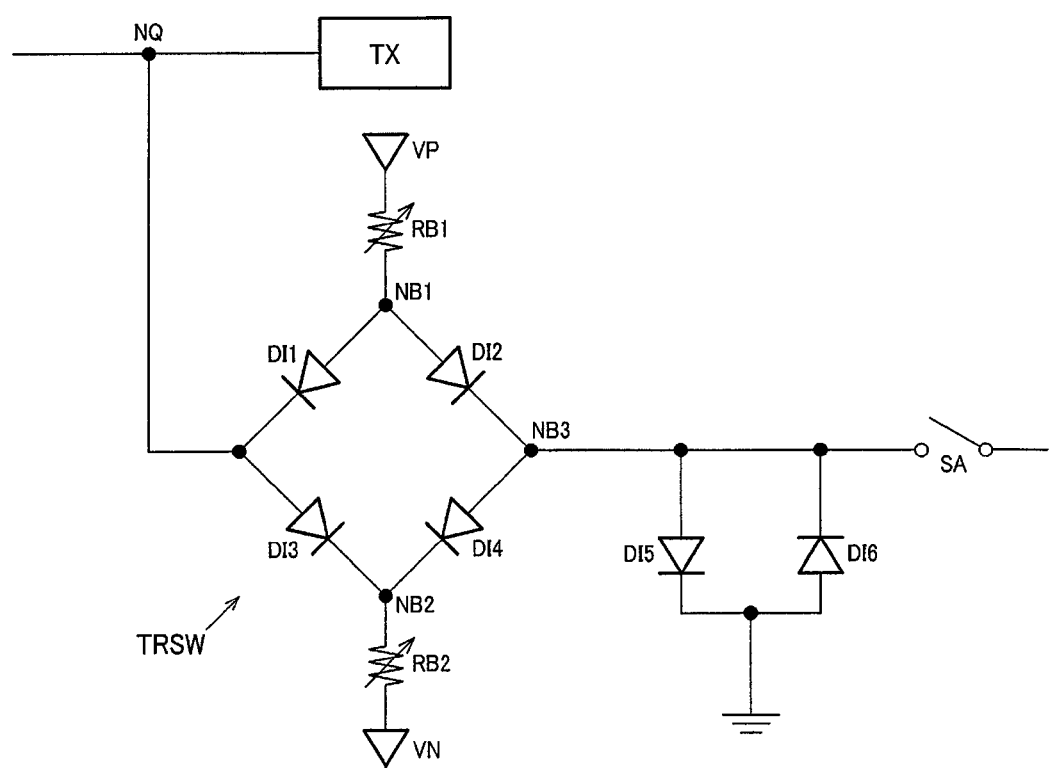
FIG. 9 is a configuration example of a transmission and reception switching circuit.

FIG. 9 illustrates a configuration example of the transmission and reception switching circuits TRSW (TRSW1 to TRSW64). The transmission and reception switching circuits TRSW have resistors RB1 and RB2 and diodes DI1 to DI6.

The resistor RB1 is provided between a high potential side power source VP and a node NB1 and the resistor RB2 is provided between a node NB2 and a low potential side power source VN.

The diode DI1 is provided between the node NB1 and output nodes NQ (NQ1 to NQ64) of the transmitting circuit TX and is a diode which sets the direction from the node NB1 to NQ as the forward direction. The diode DI2 is provided between the node NB1 and the node NB3 where one end of the switching elements SA (SA1 to SA64) is connected and is a diode which sets the direction from the node NB1 to NB3 as the forward direction. The diode DI3 is provided between the output node NQ and the node NB2 and is a diode which sets the direction from the node NQ to NB2 as the forward direction. The diode DI4 is provided between the node NB3 and the node NB2 and, in a case where power is supplied to the node, performs a circuit operation where the transmission signals are prevented (suppressed) from being transferred to the receiving circuit 150 by a clamp process or the like being performed on the voltage of the transmission signal. Here, the transmission and reception switching circuits TRSW are not limited to the circuit configuration of FIG. 9, and the transmission and reception switching circuits TRSW may be realized by analog switching elements or the like such as a transfer gate.

6. Fourth Configuration Example

Figure 10:
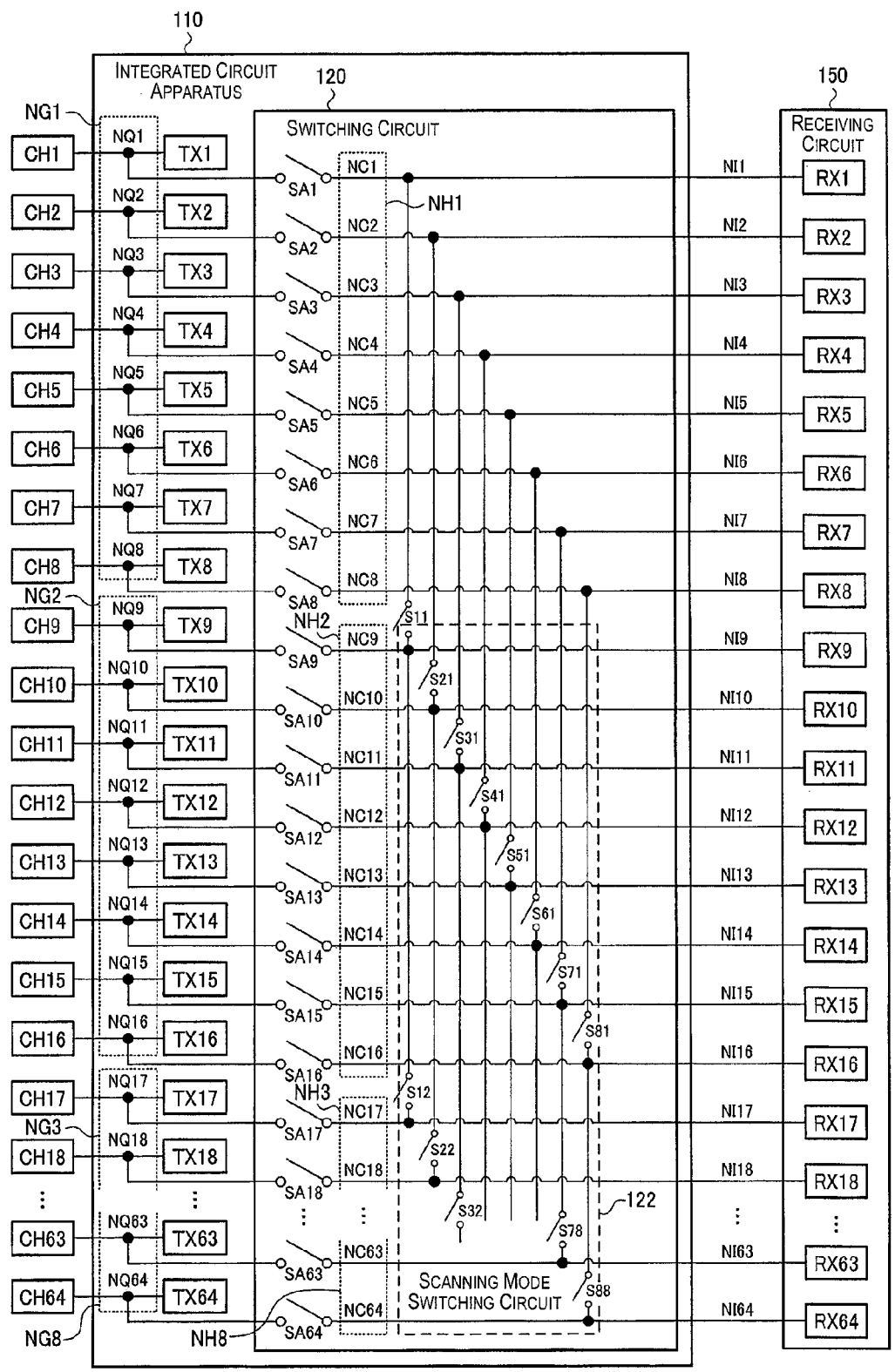
FIG. 10 is a detailed fourth configuration example of the present embodiment.

FIG. 10 illustrates a detailed fourth configuration example of the present embodiment. The fourth configuration example in FIG. 10 illustrates an example of the switching circuit 120 which realizes both of the linear scanning mode and the sector scanning mode. In the fourth configuration example in FIG. 10, a switching operation where the constituent components of a switching circuit 122 of the scanning mode are connected with regard to connection nodes (NC9 to NC16, NC17 to NC24, NC25 to NC32, . . . , NC57 to NC64) which correspond to each of the connection nodes (NC1 to NC8) among the constituent components.

In detail, the scanning mode switching circuit 122 performs a switching operation where the connection node NC1 of a connection node group NH1 is connected with the connection nodes NC9, NC17, NC25, . . . , and NC57 of the connection node groups NH2 to NH8. The switching operation is realized using switching elements S11, S12, S13, . . . , and S18 of the scanning mode switching circuit 122. For example, the connection node NC1 is connected with the connection nodes NC9, NC17, NC25, . . . , and NC57 by turning on the switching elements S11 to S18.

In addition, the scanning mode switching circuit 122 performs a switching operation where the connection node NC2 of the connection node group NH1 is connected with connection nodes NC10, NC18, NC26, . . . , and NC58 of the connection node groups NH2 to NH8. The switching operation is realized by the switching elements S21, S22, S23, . . . , and S28 of the scanning mode switching circuit 122. For example, the connection node NC2 is connected with connection nodes NC10, NC18, NC26, . . . , and NC58 by turning on the switching elements S21 to S28.

In addition, the scanning mode switching circuit 122 performs a switching operation where the connection node NC3 of the connection node group NH1 is connected with the connection nodes NC11, NC19, NC27, . . . , and NC59 of the connection node groups NH2 to NH8. The switch operation is realized using the switching elements S31, S32, S33, . . . , and S38 of the scanning mode switching circuit 122. For example, when the switching elements S31 to S38 are turned on, the connection node NC3 is connected with the connection nodes NC11, NC19, NC27, . . . , and NC59. The same also applies to the connection between the connection nodes NC4 to NC8 of the connection node group NH1 and the other connection nodes of the connection node groups NH2 to NH8.

In the fourth configuration example in FIG. 10, by turning on the switching elements S11 to S88 (S11 to S18, S21 to S28, . . . , S81 to S88) in the scanning mode switching circuit 122, the connection configuration between the switching elements SA1 to SA64 and the input nodes NI1 to NI8 of the receiving circuit 150 is the same as the connection configuration in FIG. 5. That is, the connection configuration is a connection configuration which is equivalent to the circuit in FIG. 5. Accordingly, it is possible to realize the channel selection in the linear scanning mode using the same operation as the operation which is described in FIG. 5 by turning on the switching elements S11 to S88 in the scanning mode switching circuit 122 in the linear scanning mode. Then, it is possible to input the reception signals from the eight (L) channels, which are the target of the linear scanning which are selected from among the channels CH1 to CH64, to the input nodes NI1 to NI8 in the receiving circuit 150.

On the other hand, the switching elements S11 to S88 in the scanning mode switching circuit 122 are turned off in the sector scanning mode. Then, the transfer of the transmission signal to the receiving circuit 150 is prevented and the transmission and reception switching function is realized by turning off the switching elements SA1 to SA64 in the transmitting period. In addition, the switching elements SA1 to SA64 are all turned on in the receiving period. Due to this, the reception signals from the channels CH1 to CH64 are input as is to the receiving sections RX1 to RX64 in the receiving circuit 150 via the switching elements SA1 to SA64 of the switching circuit 120. Then, the receiving sections RX1 to RX64 perform a receiving process on the reception signals from the channels CH1 to CH64.

That is, in the fourth configuration example in FIG. 10, the receiving sections RX1 to RX64 are provided for 64 channels in order to realize the sector scanning mode. Then, in the same manner as the first configuration example in FIG. 5, the receiving sections RX1 to RX8 among the receiving sections RX1 to RX64 perform a receiving process on the reception signals from the channels which are selected by the linear scanning in the linear scanning mode. On the other hand, by turning on all of the switching elements SA1 to SA64 in sector scanning mode, a receiving process is performed on the reception signals by the reception signals from the channels CH1 to CH64 being input to the receiving sections RX1 to RX64.

According to the fourth configuration example in FIG. 10, it is possible to realize an ultrasound measuring apparatus with high versatility as above since it is possible to realize the sector scanning mode in addition to the linear scanning mode which is realized using the first configuration example and the like in FIG. 5.

Here, the configuration of the present embodiment is not limited to the first to fourth configuration examples described above and various modifications are possible. For example, modifications where the first to fourth configuration examples are combined are also possible. For example, modifications are possible in the fourth configuration example in FIG. 4 where an amplification circuit (LNA) for amplifying the reception signals is provided at a stage behind the switching elements SA1 to SA64, the transmission and reception switching circuit is provided at a stage in front of the switching elements SA1 to SA64, or the like.

7. Ultrasound Transducer Element

Figure 11A:
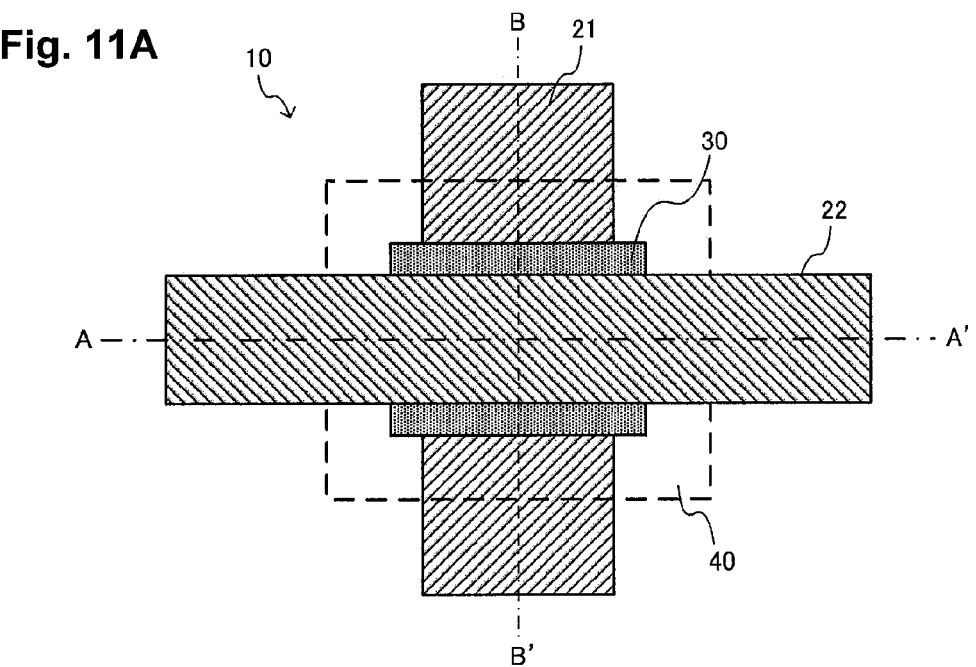
FIG. 11A to FIG. 11C are configuration examples of ultrasound transducer elements.
Figure 11B:
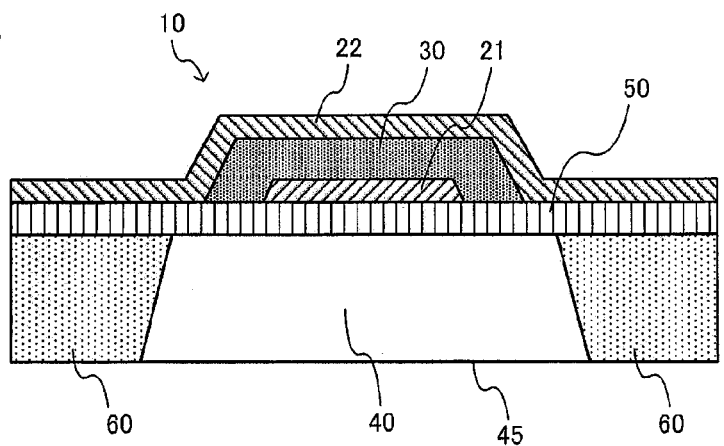
Figure 11C:
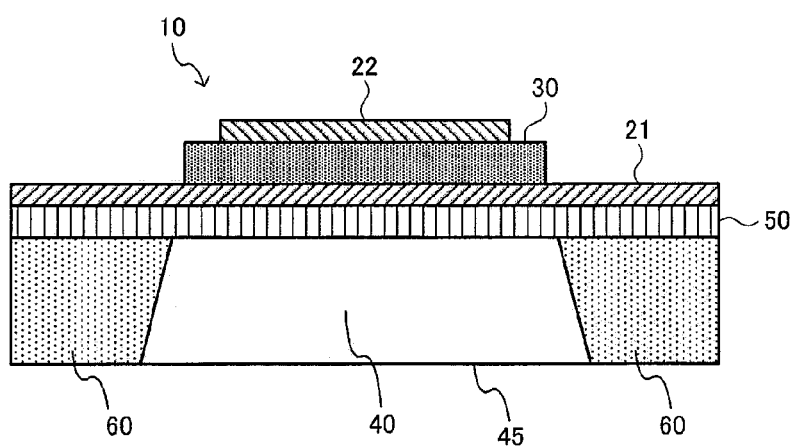

FIG. 11A to FIG. 11C illustrate a configuration example of an ultrasound transducer element 10 of the ultrasound transducer device 100. The ultrasound transducer element 10 has a diaphragm (a membrane and a support member) 50 and a piezoelectric element section. The piezoelectric element section has a first electrode layer (a lower electrode) 21, a piezoelectric layer (a piezoelectric film) 30, and a second electrode layer (an upper electrode) 22.

FIG. 11A is a planar diagram of the ultrasound transducer element 10 which is formed on the substrate (a silicon substrate) 60 viewed from a direction which is orthogonal to a substrate 60 on the element forming surface side. FIG. 11B is a cross sectional diagram illustrating a cross section along A-A' in FIG. 11A. FIG. 11C is a cross sectional diagram illustrating a cross section along B-B' in FIG. 11A.

The first electrode layer 21 is formed by, for example, a metal thin film on the upper layer of the diaphragm 50. The first electrode layer 21 may be wiring which extends to the outside of an element forming region as shown in FIG. 11A and is connected with the ultrasound transducer element 10 which is adjacent.

The piezoelectric layer 30 is formed, for example, by a PZT (lead zirconate titanate) film and is provided to cover at least a portion of the first electrode layer 21. Here, the material of the piezoelectric layer 30 is not limited to PZT and, for example, lead titanate (PbTiO3), lead zirconate (PbZrO3), lead lanthanum titanate ((Pb, La) TiO3), or the like may be used.

For example, the second electrode layer 22 is formed by a metal thin film and is provided so as to cover at least a portion of the piezoelectric layer 30. The second electrode layer 22 may be wiring which extends to the outside of the element forming region as shown in FIG. 11A and is connected with the ultrasound transducer element 10 which is adjacent.

The diaphragm (membrane) 50 is provided so as to close off an opening 40 using a two layer structure of, for example, an SiO2 thin film and ZrO2 thin film. It is possible for the diaphragm 50 to support the piezoelectric layer 30 and the first and second electrode layers 21 and 22, to vibrate according to expansion and contraction of the piezoelectric layer 30 and to generate ultrasound.

The opening (cavity region) 40 is arranged in an array formation on the substrate 60. The opening 40 is formed by etching using reactive ion etching (RIE) or the like from the rear surface (the side where the elements are not formed) side of the substrate 60 (silicon substrate). The resonance frequency of the ultrasound is determined according to the size of an opening section 45 of the opening 40 and the ultrasound is irradiated to the piezoelectric layer 30 side (the front direction from the back of the paper surface in FIG. 11A).

The lower electrode (the first electrode) of the ultrasound transducer element 10 is formed by the first electrode layer 21 and the upper electrode (the second electrode) is formed by the second electrode layer 22. In detail, a portion, which is covered by the piezoelectric layer 30, of the first electrode layer 21 forms the lower electrode and a portion, which covers the piezoelectric layer 30, of the second electrode layer 22 forms the upper electrode. That is, the piezoelectric layer 30 is provided to be interposed by the lower electrode and the upper electrode.

The piezoelectric layer 30 is expanded and contracted in an in-plane direction by voltage being applied between the lower electrode and the upper electrode, that is, between the first electrode layer 21 and the second electrode layer 22. One surface of the piezoelectric layer 30 is bonded with the diaphragm 50 via the first electrode layer 21, but while the second electrode layer 22 is formed on the other surface, other layers are not formed on the second electrode layer 22. As a result, the diaphragm 50 side of the piezoelectric layer 30 does not easily expand and contract and the second electrode layer 22 side easily expands and contracts. Accordingly, when voltage is applied to the piezoelectric layer 30, bending is generated to make the opening 40 side convex and the diaphragm 50 bends. By applying an AC voltage to the piezoelectric layer 30, the diaphragm 50 vibrates in the film thickness direction and ultrasound is irradiated due to the vibration of the diaphragm 50.

The voltage which is applied to the piezoelectric layer 30 is, for example, 10 to 30 V, and the frequency is, for example, 1 to 10 MHz. That is, it is possible to perform driving at a low voltage compared to a case where bulk piezoelectric elements are used and it is possible to manufacture a driving IC using a semiconductor process with a low breakdown voltage. Due to this, it is possible to make the ultrasound measuring apparatus compact and increase the number of channels.

In addition, the ultrasound transducer element 10 also operates as a reception element which receives an ultrasound echo where the ultrasound which is emitted is reflected by the target and returned. The diaphragm 50 vibrates according to the ultrasound echo, and stress is applied to the piezoelectric layer 30 due to the vibration and a voltage is generated between the lower electrode and the upper electrode. It is possible to extract the voltage as a reception signal.

8. Ultrasound Transducer Device

Figure 12:
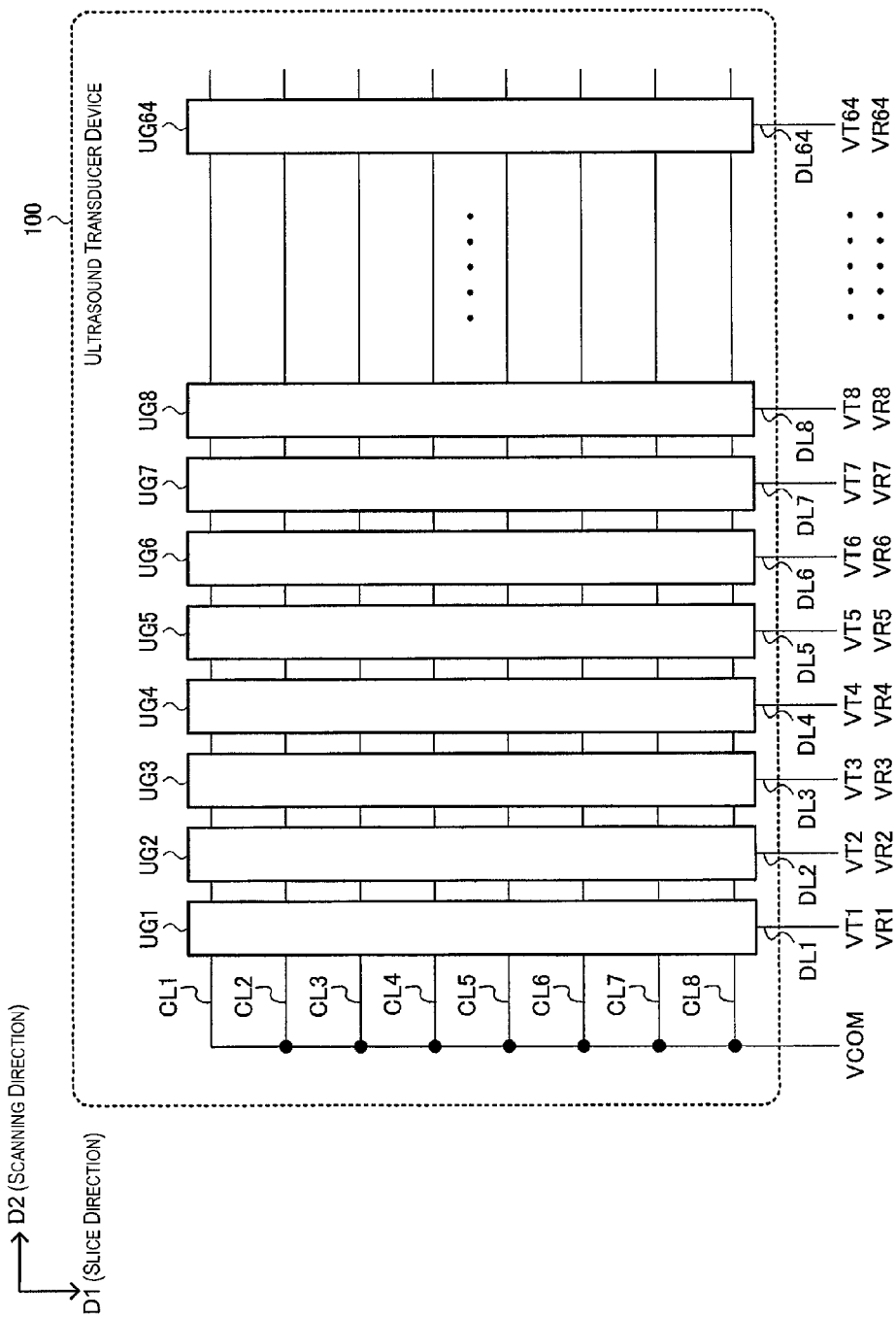
FIG. 12 is a configuration example of an ultrasound transducer device.

FIG. 12 illustrates a configuration example of the ultrasound transducer device 100 (an element chip). The ultrasound transducer device 100 of the present configuration example includes a plurality of ultrasound transducer element groups UG1 to UG64, driving electrode lines DL1 to DL64 (broadly defined as first to $n^{th}$ driving electrode lines where n is an integer of 2 or more), and common electrode lines CL1 to CL8 (broadly defined as first to $m^{th}$ common electrode lines where m is an integer of 2 or more). Here, the number of lines (n) of the driving electrode lines and the number of lines (m) of the common electrode lines are not limited to the numbers of lines shown in FIG. 12.

The plurality of ultrasound transducer elements UG1 to UG64 are arranged in 64 rows along a second direction D2 (scanning direction). Each of the ultrasound transducer element groups UG1 to UG64 has a plurality of ultrasound transducer elements which are arranged along a first direction D1 (slice direction).

Figure 13A:
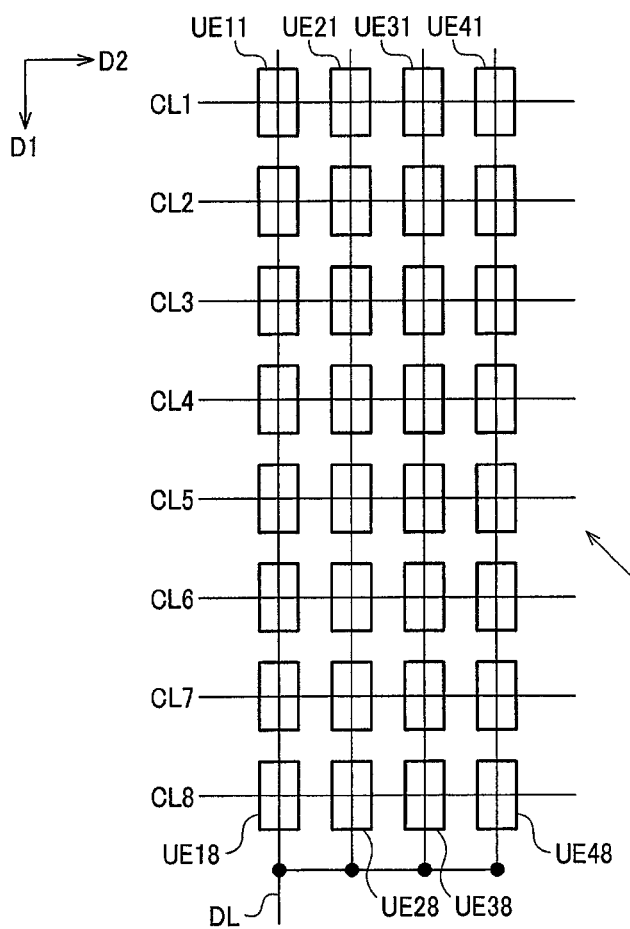
FIG. 13A and FIG. 13B are configuration examples of ultrasound transducer element groups which are provided to correspond to each of the channels.

FIG. 13A illustrates an example of the ultrasound transducer element groups UG (UG1 to UG64). In FIG. 13A, the ultrasound transducer element groups UG are configured by first to fourth element rows. The first element row is configured by ultrasound transducer elements UE11 to UE18 which are arranged along the first direction D1 and the second element row is configured by ultrasound transducer elements UE21 to UE28 which are arranged along the first direction D1. The same also applies to the third element row (UE31 to UE38) and the fourth element row (UE41 to UE48). The first to fourth element rows are commonly connected with the driving electrode lines DL (DL1 to DL64). In addition, the ultrasound transducer elements of the first to fourth element rows are connected with the common electrode lines CL1 to CL8.

Figure 13B:
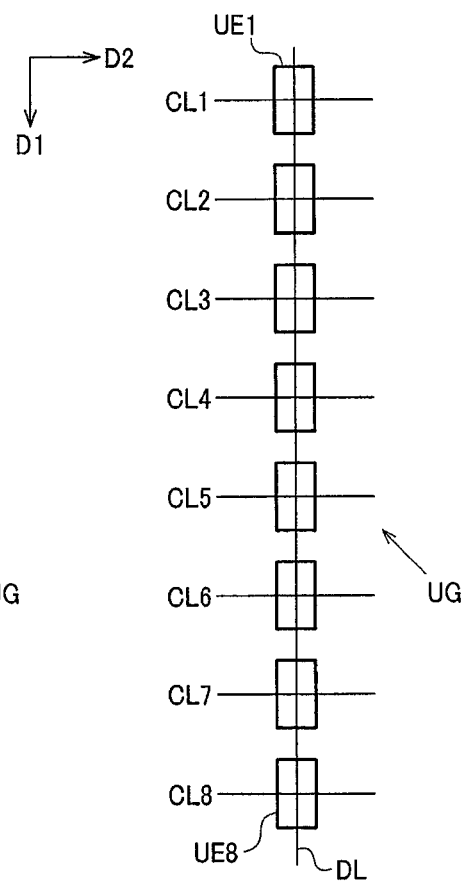

Then, the ultrasound transducer element groups UG of FIG. 13A configure one channel of the ultrasound transducer device. That is, the driving electrode lines DL are equivalent to the driving electrode lines of one channel and the transmission signals of one channel from the transmitting circuit are input to driving electrode lines DL. In addition, the reception signals of one channel from the driving electrode lines DL are output from the driving electrode lines DL. Here, the number of element rows which configure one channel is not limited to 4 rows as in FIG. 13A and may be less than 4 rows or may be greater than 4 rows. For example, the number of element rows may be one row as shown in FIG. 13B.

As shown in FIG. 12, the driving electrode lines DL1 to DL64 (the first to $n^{th}$ driving electrode lines) are wired along the first direction D1. A $j^{th}$ (j is an integer where 1≤j≤n) driving electrode line DLj ($j^{th}$ channel) among the driving electrode lines DL1 to DL64 is connected with the first electrode (for example, the lower electrode) which has the ultrasound transducer element of a $j^{th}$ ultrasound transducer element group UGj.

In the transmitting period where the ultrasound is emitted, transmission signals VT1 to VT64 are supplied to the ultrasound transducer element via the driving electrode lines DL1 to DL64. In addition, in the receiving period where the ultrasound echo signal is received, reception signals VR1 to VR64 from the ultrasound transducer element are output via the driving electrode lines DL1 to DL64.

The common electrode lines CL1 to CL8 (the first to $m^{th}$ common electrode lines) are wired along the second direction D2. The second electrode of the ultrasound transducer element is connected with any of the common electrode lines CL1 to CL8. In detail, for example, an $i^{th}$ (i is an integer where 1≤i≤m) common electrode line CLi among the common electrode lines CL1 to CL8 is connected with the second electrode (for example, the upper electrode) which has the ultrasound transducer element which is arranged in the $i^{th}$ column as shown in FIG. 12.

A common voltage VCOM is supplied to the common electrode lines CL1 to CL8. It is sufficient if the common voltage VCOM is a constant DC voltage, and it is sufficient if the common voltage VCOM is not 0 V, that is, a ground potential.

Then, a voltage which is the difference between the transmission signal voltage and the common voltage is applied to the ultrasound transducer element and ultrasound is irradiated at a predetermined frequency in the transmitting period.

Here, the arrangement of the ultrasound transducer elements may be a so-called staggered arrangement or the like without being limited to the matrix arrangement shown in FIG. 12.

In addition, FIG. 11A to FIG. 13B illustrate a case where one ultrasound transducer element is used as both the transmission element and the reception element, but the present embodiment is not limited to this. For example, an ultrasound transducer element for the transmitting element and an ultrasound transducer element for the reception element may be provided separately and arranged in an array formation.

9. Ultrasound Measuring Apparatus

Figure 14:
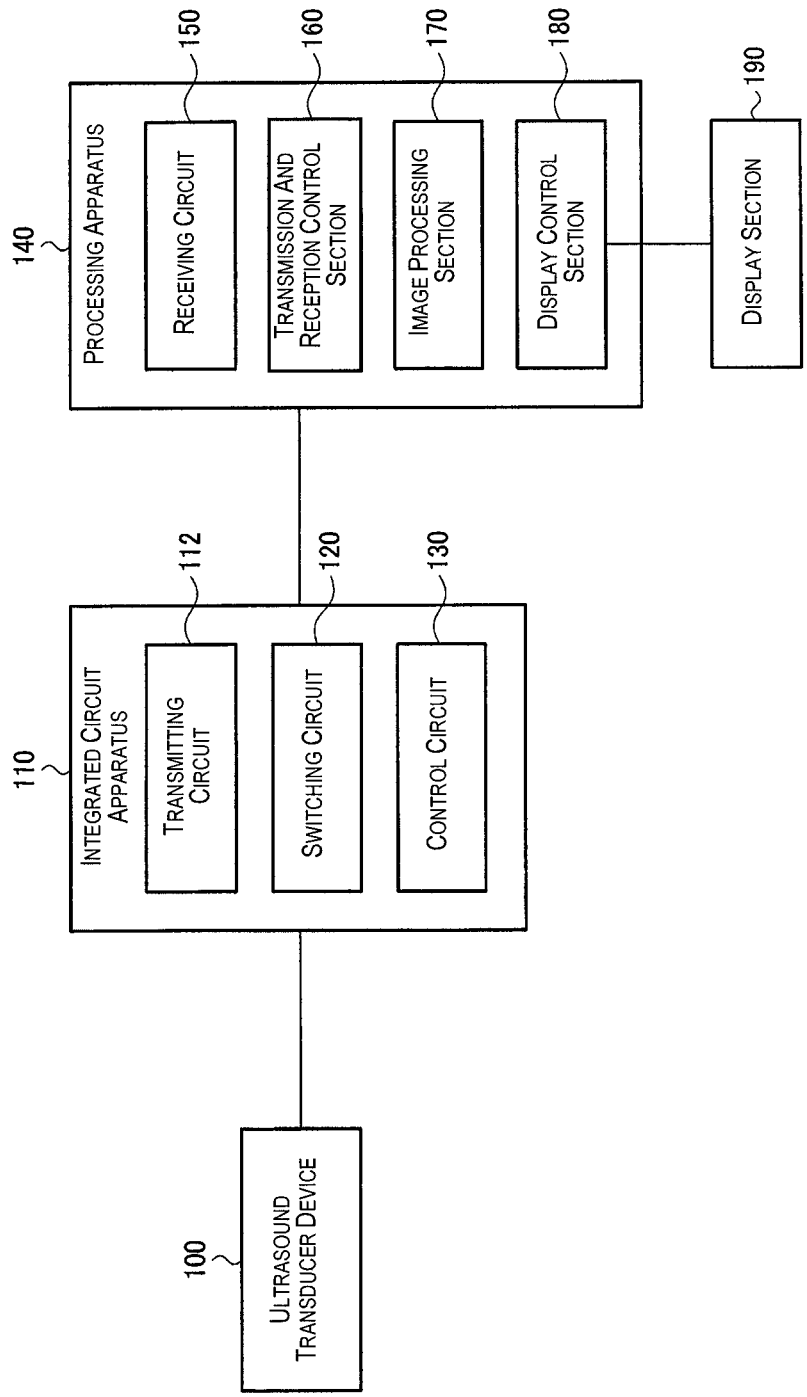
FIG. 14 is a configuration example of an ultrasound measuring apparatus (ultrasound diagnostic apparatus) of the present embodiment.

FIG. 14 is a block diagram illustrating an overall configuration of the ultrasound measuring apparatus (the ultrasound diagnostic apparatus) of the present embodiment. The ultrasound measuring apparatus in FIG. 14 includes the ultrasound transducer device 100 and the integrated circuit apparatus 110. In addition, it is possible to include a processing apparatus 140. For example, in a case where the ultrasound measuring apparatus is used as the ultrasound diagnostic apparatus, it is possible for the ultrasound diagnostic apparatus to include a display section 190. Here, the ultrasound measuring apparatus of the present embodiment is not limited to the configuration of FIG. 14, and various modifications which omit a portion of the constituent components, substitute with other constituent components, add other constituent components, or the like are possible.

The integrated circuit apparatus 110 includes transmitting circuits 112 (TX1 to TX64), the switching circuit 120, and the control circuit 130 described above. The integrated circuit apparatus 110 is a semiconductor IC (a semiconductor chip) which is formed by, for example, a CMOS process.

The processing apparatus 140 performs various types of control processes on the ultrasound measuring apparatus, ultrasound transmission and reception control, and the like. The processing apparatus 140 includes the receiving circuit 150, a transmission and reception control section 160, an image processing section 170, and a display control section 180.

The receiving circuit 150 performs receiving processes and has a plurality of receiving sections RX which are described in FIG. 6. The receiving sections RX are analog front-end circuits (AFE) which are provided for each of the channels. The transmission and reception control section 160 performs various types of control for transmitting and receiving ultrasound. For example, the transmission and reception control section 160 performs a control process of a transmission beam former, a control process of a reception beam former, and the like. Based on the ultrasound reception signals (A mode waveform data), the image processing section 170 generates images such as B mode images and performs various types of imaging processes with regard to the images which are generated. The display control section 180 performs control for displaying the images or the like which are generated using the ultrasound reception signals on the display section 190.

The ultrasound probe of the present embodiment includes the ultrasound measuring apparatus. In this case, the ultrasound probe may include only the ultrasound transducer device 100 and the integrated circuit apparatus 110 in FIG. 14, or may include the processing apparatus 140 and the display section 190 in addition to the ultrasound transducer device 100 and the integrated circuit apparatus 110.

FIG. 15A to FIG. 15D are diagrams which describe examples of specific embodiments of the ultrasound measuring apparatus. In FIG. 15A, flexible printed circuits 210 and 212 are connected with regard to the ultrasound transducer device 100. The integrated circuit apparatus 110 of the present embodiment is mounted on the flexible printed circut 210. The ultrasound transducer device 100 has a plurality of terminals (channel terminals) which are arranged along the long side of the ultrasound transducer device 100 and the integrated circuit apparatus 110 also has a plurality of terminals (channel terminals) which are arranged along the long side of the integrated circuit apparatus 110. Then, the plurality of terminals of the ultrasound transducer device 100 and a plurality of terminals of the integrated circuit apparatus 110 are connected using a plurality of signal lines which are formed on the flexible printed circut 210. The plurality of signal lines are wired along a first direction DR1. The integrated circuit apparatus 110 is mounted on the flexible printed circut 210 such that the direction of the long side of the integrated circuit apparatus 110 is along a second direction DR2 which is orthogonal to (intersecting with) the first direction DR1.

Here, the plurality of terminals of the integrated circuit apparatus 110 are, for example, bump terminals. In addition, it is possible to realize the mounting of the integrated circuit apparatus 110 on the flexible printed circut 210 by flip chip mounting (bare chip mounting) which uses, for example, an anisotropic conductive film (ACF) or the like. In addition, in FIG. 15A, the integrated circuit apparatus 110 is mounted only on the flexible printed circut 210, but the integrated circuit apparatus 110 may be mounted on both the flexible printed circuits 210 and 212. For example, a first integrated circuit apparatus is mounted on the flexible printed circut 210 and a second integrated circuit apparatus is mounted on the flexible printed circut 212.

In this case, in the ultrasound transducer device 100, a first terminal group is provided to be electrically connected via signal lines with a terminal group of the first integrated circuit apparatus which is mounted on the flexible printed circut 210 is provided. In addition, a second terminal group is provided to be connected via signal lines with a terminal group of the second integrated circuit apparatus which is mounted on the flexible printed circut 212. Then, the transmission signals from the first integrated circuit apparatus are input to the first terminal group of the ultrasound transducer device 100 and the reception signals are output to the first integrated circuit apparatus from the first terminal group. In addition, the transmission signals from the second integrated circuit apparatus are input to the second terminal group of the ultrasound transducer device 100 and the reception signals are output to the second integrated circuit apparatus from the second terminal group.

FIG. 15B is a cross sectional diagram illustrating a configuration example of the ultrasound probe 200 of the present embodiment. In FIG. 15B, the flexible printed circuits 210 and 212 are connected with regard to the ultrasound transducer device 100 as in FIG. 15A and the integrated circuit apparatus 110 is mounted on the flexible printed circut 210. An acoustic matching layer (an acoustic lens) 102 is provided on the surface side of the ultrasound transducer device 100. A back plate 104 is provided on the rear surface side of the ultrasound transducer device 100. The ultrasound transducer device 100 (and the back plate) is supported by a support member 106 which is attached to circuit substrates 220 and 222.

The circuit substrates 220 and 222 are, for example, rigid substrates (print substrates). The circuit substrate 220 and the circuit substrate 222 are connected with signal lines via a connector 224. Then, the flexible printed circut 210 is connected with the ultrasound transducer device 100 and the circuit substrate 220. In addition, the flexible printed circut 212 is connected with the ultrasound transducer device 100 and the circuit substrate 222.

The circuit substrates 220 and 222 are mounted with, for example, an IC (an integrated circuit apparatus) or the like which realizes a portion or all of the processing apparatus 140 in FIG. 14. For example, an IC or the like which realizes at least the receiving circuit 150 is mounted on the circuit substrate 220. In addition, an IC or the like which realizes the transmission and reception control section 160, the image processing section 170, and the display control section 180 is mounted on the circuit substrates 220 and 222.

In this manner, in FIG. 15A and FIG. 15B, since the integrated circuit apparatus 110 which has the transmitting circuit 112 and the switching circuit 120 is mounted on the flexible printed circut 210, it is possible to suppress transmission loss and the like of the transmission signal to a minimum. On the other hand, it is possible for the receiving circuit 150 which is configured by an analog circuit to realize performance maintenance of the analog circuit and a stabilized analog circuit operation by being mounted on the circuit substrate 220 which is a rigid substrate.

In FIG. 15C, the integrated circuit apparatus 110 is not mounted on the flexible printed circuits 210 and 212, but the integrated circuit apparatus 110 is mounted on the circuit substrate 220 as shown in FIG. 15D. Then, the ultrasound probe 200 (the circuit substrates 220 and 222) is connected with the body apparatus 250 of the ultrasound measuring apparatus (the ultrasound diagnostic apparatus) via the cable 240 (a coaxial cable). That is, FIG. 15B is an example of an integrated type of probe and body and FIG. 15D is an example of a separated type of probe and body. The integrated type in FIG. 15B has an advantage that it is possible to have a compact device configuration. The separated type in FIG. 15D has an advantage that it is possible to process even processes with a heavy load using the body apparatus 250. Here, in FIG. 15B and FIG. 15D, the circuit substrates 220 and 222 have a two substrate configuration, but the circuit substrates may be configured by one substrate, or may be configured by three or more substrates.

FIG. 16A to FIG. 16C are examples of specific device configurations of the ultrasound measuring apparatuses (broadly defined as electronic devices) of the present embodiment. FIG. 16A is an example of a hand-held version of the ultrasound measuring apparatus 400 and FIG. 16B is an example of a stationary version of the ultrasound measuring apparatus 400. FIG. 16C is an example of an integrated version of the ultrasound measuring apparatus 400 where an ultrasound probe 300 is built into the body.

The ultrasound measuring apparatus 400 in FIG. 16A and FIG. 16B includes the ultrasound probe 300 and a body apparatus 401 and the ultrasound probe 300 and the body apparatus 401 are connected using a cable 312. The lead end portion of the ultrasound probe 300 is provided with a probe head 320 and the body apparatus 401 is provided with a display section 440 which displays images. In FIG. 16C, the ultrasound probe 300 is built into the ultrasound measuring apparatus 400 which has the display section 440. In the case of FIG. 16C, it is possible to realize the ultrasound measuring apparatus 400 using, for example, a general-purpose portable information terminal such as a smart phone.

Here, the present embodiment was described in detail as above, but a person skilled in the art will easily be able to understand that numerous modifications are possible which substantially do not depart from the novel items and effects of the present invention. Accordingly, the modified examples are all included in the scope of the present invention. For example, it is possible to replace the terms (the transmitting circuits TX1 to TX64, the output nodes NQ1 to NQ64, the channels CH1 to CH64, the input nodes NI1 to NI8, and the like) described in the specification or the diagrams with different terms with the same or a broader meaning (the first to $K^{th}$ transmitting circuits, the first to $K^{th}$ output nodes, the first to $K^{th}$ channels, the first to $L^{th}$ input nodes, and the like) at least once in any place in the specification or the diagrams. In addition, the configuration and the operation of the integrated circuit apparatus, the ultrasound measuring apparatus, the ultrasound probe, the ultrasound transducer device, the ultrasound transducer element, and the like are not limited to the configurations and the operations which are described above in the present embodiment, and various modifications are possible.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An integrated circuit apparatus comprising:
a first transmitting circuit to a $K^{th}$ transmitting circuit, where K is an integer of 3 or more, configured and arranged to output transmission signals to a first channel to a $K^{th}$ channel of an ultrasound transducer device having a plurality of ultrasound transducer elements;
a receiving circuit including a first input node to an $L^{th}$ input node, where L is an integer of 2 or more with L<K;
a switching circuit configured and arranged to perform a switching operation; and
a control circuit configured and arranged to perform switching control of the switching circuit,
wherein the switching circuit includes a first switching element to a $K^{th}$ switching element which are provided between the receiving circuit and a first output node to a $K^{th}$ output node of the first transmitting circuit to the $K^{th}$ transmitting circuit and are on-off controlled by the control circuit,
wherein each of the first input node to the $L^{th}$ input node of the receiving circuit is branched to be connected to the switching elements separated from each other,
wherein the control circuit is configured to control the switching circuit to perform an operation wherein:
switching elements are selectively turned off in a transmitting period so that signal transfer of the transmission signals from the first transmitting circuit to the $K^{th}$ transmitting circuit to the receiving circuit is not performed during the transmitting period, and
wherein the switching operation comprises of selectively controlling the switching elements so that a reception signal from a channel which is partially selected from among the first channel to the $K^{th}$ channel is output to the receiving circuit in a receiving period,
wherein the first switching element to the $L^{th}$ switching element among the first switching element to the $K^{th}$ switching element are selected and separately operated, and the switching elements that are not selected are off, and wherein only one of the branched switching elements connected to the same input node is on, and the other branched switching elements connected to the same input node are off.

2. The integrated circuit apparatus according to claim 1, wherein
the switching circuit is configured and arranged to perform the switching operation where a plurality of channels which are a target of linear scanning from among the first channel to the $K^{th}$ channel are sequentially shifted and selected in the receiving period in a linear scanning mode.

3. The integrated circuit apparatus according to claim 2, wherein
the switching circuit is configured and arranged to output the reception signal from L channels, which are a target of the linear scanning which are selected from among the first channel to the $K^{th}$ channel, to the first input node to the $L^{th}$ input node of the receiving circuit in the receiving period in the linear scanning mode, and
the switching circuit is configured and arranged to output the reception signal from the first channel to the $K^{th}$ channel to the first input node to the $K^{th}$ input node of the receiving circuit in the receiving period in a sector scanning mode.

4. The integrated circuit apparatus according to claim 1, wherein the first output node to the $K^{th}$ output node are grouped into a first output node group to an $M^{th}$ output node group where each of the output node groups is configured by L output nodes, where L and M are integers of 2 or more with L<and M<K,
the first switching element to the $K^{th}$ switching element are grouped into a first switching element group to an $M^{th}$ switching element group where each of the switching element groups is configured by L switching elements, and
an $i^{th}$ switching element group, where 1≤i≤M, among the first switching element group to the $M^{th}$ switching element group is provided between an $i^{th}$ output node group among the first output node group to the $M^{th}$ output node group and the first input node to the $L^{th}$ input node of the receiving circuit.

5. The integrated circuit apparatus according to claim 4, wherein the control circuit is configured and arranged to perform the switching control by turning off the first switching element to the $K^{th}$ switching element in the transmitting period, and
the control circuit is configured and arranged to perform the switching control which sequentially shifts and selects L switching elements which are the target of the linear scanning from among the first switching element to the $K^{th}$ switching element and turns on the selected L switching elements in the receiving period.

6. The integrated circuit apparatus according to claim 5, further comprising
a first amplification circuit to an $L^{th}$ amplification circuit configured and arranged to perform signal amplification of the reception signal from the selected L switching elements and to output the reception signal after signal amplification to the first input node to the $L^{th}$ input node of the receiving circuit.

7. The integrated circuit apparatus according to claim 4, further comprising
a first transmission and reception switching circuit to a $K^{th}$ transmission and reception switching circuit provided between the first output node to the $K^{th}$ output node and the first switching element to the $K^{th}$ switching element, and configured and arranged to set the signal transfer of the transmission signals from the first transmitting circuit to the $K^{th}$ transmitting circuit to the receiving circuit to be not performed in the transmitting period, wherein the control circuit is configured and arranged to perform the switching control which sequentially shifts and selects L switching elements which are a target of linear scanning from among the first switching element to the $K^{th}$ switching element and turns on the selected L switching elements in the receiving period.

8. The integrated circuit apparatus according to claim 4, wherein the switching circuit includes a scanning mode switching circuit, the first switching element to the $K^{th}$ switching element are provided between the first output node to the $K^{th}$ output node and a first connection node to a $K^{th}$ connection node, the first connection node to the $K^{th}$ connection node are grouped into a first connection node group to an $M^{th}$ connection node group where each of the connection node groups is configured by L connection nodes, and the scanning mode switching circuit is configured and arranged to perform a switching where each of the connection nodes of the first connection node group are connected with regard to connection nodes which correspond to each of the connection nodes among the second connection node group to the $M^{th}$ connection node group in a linear scanning mode.

9. The integrated circuit apparatus according to claim 1, wherein the first transmitting circuit to the $K^{th}$ transmitting circuit are configured and arranged to output the transmission signals with regard to the first channel to the $K^{th}$ channel without going through a multiplexer.

10. An ultrasound measuring apparatus comprising:

the integrated circuit apparatus according to claim 1; and the ultrasound transducer device having the plurality of ultrasound transducer elements, wherein each of the ultrasound transducer elements has:

a diaphragm which closes off each opening of a plurality of openings formed in a substrate, and a piezoelectric element section provided with a lower electrode, an upper electrode, and a piezoelectric film provided on the diaphragm.

11. The ultrasound measuring apparatus according to claim 10, wherein the integrated circuit apparatus is mounted on a flexible printed substrate connected with the ultrasound transducer device.

12. The ultrasound measuring apparatus according to claim 11, further comprising a printed circuit board where the receiving circuit is mounted, wherein the flexible printed substrate is connected with the ultrasound transducer device and the printed circuit board.

13. An ultrasound probe comprising:

the integrated circuit according to claim 1; and the ultrasound transducer device having the plurality of ultrasound transducer elements.

14. An ultrasound diagnostic apparatus comprising:

the ultrasound measuring apparatus according to claim 10; and a display section configured and arranged to display an image.

* * * * *